(12) United States Patent
Jensen et al.

(10) Patent No.: US 10,066,245 B2
(45) Date of Patent: Sep. 4, 2018

(54) MICROBIAL PRODUCTION OF 3-HYDROXYPROPIONIC ACID

(71) Applicant: TECHNICAL UNIVERSITY OF DENMARK, Kgs. Lyngby (DK)

(72) Inventors: Niels Bjerg Jensen, Kgs. Lyngby (DK); Irina Borodina, Kgs. Lyngby (DK); Yun Chen, Kgs. Lyngby (DK); Jerome Maury, Kgs. Lyngby (DK); Kanchana Rueksomtawin Kildegaard, Kgs. Lyngby (DK); Jochen Förster, Kgs. Lyngby (DK); Jens Nielsen, Kgs. Lyngby (DK)

(73) Assignee: TECHNICAL UNIVERSITY OF DENMARK, Kgs. Lyngby (DK)

( * ) Notice: Subject to any disclaimer, the term of this patent is extended or adjusted under 35 U.S.C. 154(b) by 0 days.

(21) Appl. No.: 14/896,897

(22) PCT Filed: Jun. 12, 2014

(86) PCT No.: PCT/EP2014/062246
§ 371 (c)(1),
(2) Date: Dec. 8, 2015

(87) PCT Pub. No.: WO2014/198831
PCT Pub. Date: Dec. 18, 2014

(65) Prior Publication Data
US 2016/0138056 A1 May 19, 2016

(30) Foreign Application Priority Data
Jun. 14, 2013 (EP) .................................... 13172149

(51) Int. Cl.
| | |
|---|---|
| *C12N 1/19* | (2006.01) |
| *C12P 7/42* | (2006.01) |
| *C12N 9/04* | (2006.01) |
| *C12N 9/02* | (2006.01) |
| *C12N 9/00* | (2006.01) |
| *C12N 15/52* | (2006.01) |
| *C12N 15/81* | (2006.01) |

(52) U.S. Cl.
CPC .............. *C12P 7/42* (2013.01); *C12N 9/0006* (2013.01); *C12N 9/0008* (2013.01); *C12N 9/93* (2013.01); *C12N 15/52* (2013.01); *C12N 15/81* (2013.01); *C12Y 101/01298* (2013.01); *C12Y 102/01075* (2013.01); *C12Y 604/01002* (2013.01); *C12Y 102/01009* (2013.01)

(58) Field of Classification Search
None
See application file for complete search history.

(56) References Cited

U.S. PATENT DOCUMENTS

| | | | | |
|---|---|---|---|---|
| 8,198,066 B2* | 6/2012 | Gokarn | ............... | C12N 9/0004 435/183 |
| 2010/0248233 A1* | 9/2010 | Muller | ................. | C07K 14/33 435/6.13 |
| 2012/0135481 A1 | 5/2012 | Jessen et al. | | |
| 2013/0066035 A1 | 3/2013 | Burgard | | |

FOREIGN PATENT DOCUMENTS

| | | |
|---|---|---|
| EP | 2505656 | 10/2012 |
| WO | 02/42418 | 5/2002 |
| WO | 2007/024718 | 3/2007 |
| WO | 2008/028002 | 3/2008 |
| WO | 2008/080124 | 7/2008 |
| WO | 2011/147818 | 12/2011 |
| WO | 2012/017083 | 2/2012 |

OTHER PUBLICATIONS

Zhou et al., Cell Mol Life Sci 63:2260-2290, 2006.*
Kozak, M., Gene 234:187-208, 1999.*
Guo et al., J. Ind. Microbiol. Biotechnol. 38:935-943, 2011.*
Shiba et al., Met. Eng. 9:160-168, 2007.*
Hugler et al., J. Bacteriol. 184:2404-2410, 2002.*
Jeffries, T., "Engineering yeasts for xylose metabolism", Curr. Opin. Biotech. 17:320-326, 2006.*
International Search Report dated Aug. 11, 2014 in International Patent Application No. PCT/EP2014/062246.
Rathnasingh, Chelladurai et al., "Production of 3-hydroxypropionic acid via malonyl-CoA pathway using recombinant *Escherichia coli* strains", Journal of Biotechnology, vol. 157, available online Jun. 25, 2011, pp. 633-640.
Verho, Ritva et al., "Identification of the First Fungal NADP-GAPDH from Kluyveromyces lactis", Biochemistry, vol. 41, Issue 46, Oct. 24, 2002, pp. 13833-13838.
Chen, Yun et al., "Enhancing the copy number of episomal *Saccharomyces cerevisiae* for improved protein", FEMS Yeast Research, vol. 12, published online Apr. 25, 2012, pp. 598-607.
Chen, Yun et al., "Establishing a platform cell factory through engineering of yeast acetyl-CoA metabolism", Metabolic Engineering, vol. 15, available online Nov. 17, 2012, pp. 48-54.
Dale, Susan et al., "Similar substrate recognition motifs for mammalian AMP-activated protein kinase, higher plant HMG-CoA reductase kinase-A, yeast SNF1, and mammalian calmodulin-dependent protein kinase I", FEBS Letters, vol. 361, pp. 191-195.
Ficarro, Scott B. et al., "Phosphoproteome analysis by mass spectrometry and its application to *Saccharomyces cerevisiae*", Nature Biotechnology, vol. 20, accepted Jan. 9, 2002, pp. 301-305.

(Continued)

*Primary Examiner* — David Steadman
(74) *Attorney, Agent, or Firm* — Pillsbury Winthrop Shaw Pittman LLP

(57) ABSTRACT

A yeast cell having a reduced level of activity of NAD dependent glyceraldehyde-3-phosphate dehydrogenase (GAPDH) has at least one exogenous gene encoding NADP dependent GAPDH and/or has up-regulation of at least one endogenous gene expressing NADP dependent GAPDH, wherein combined expression of the enzymes NADP dependent GAPDH, PDC, ALD, ACS, ACC* and MCR in said host cell increases metabolic flux towards 3-HP via malonyl-CoA compared to an otherwise similar yeast cell lacking said genetic modification.

14 Claims, 8 Drawing Sheets

Figure 1:
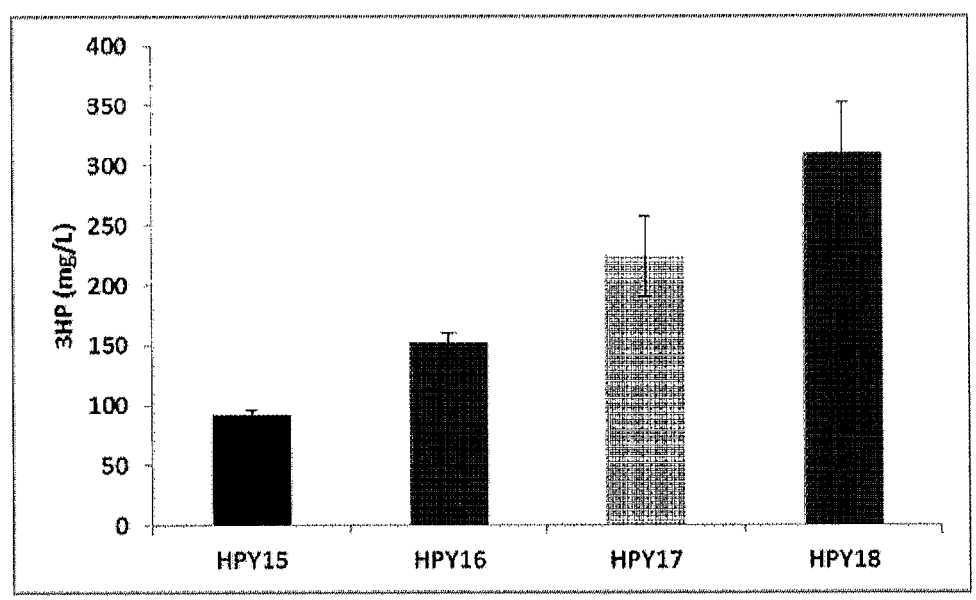

Specification includes a Sequence Listing.

(56) References Cited

OTHER PUBLICATIONS

Nielsen, Jens, "Systems biology of lipid metabolism: From yeast to human", FEBS Letters, vol. 583, available online Oct. 23, 2009, pp. 3905-3913.

Shirra, Margaret K. et al., "Inhibition of Acetyl Coenzyme A Carboxylase Activity Restores Expression of the INO1 Gene in a snf1 Mutant Strain of *Saccharomyces cerevisiae*", Molecular and Cellular Biology., vol. 21, No. 17, Sep. 2001, pp. 5710-5722.

Woods, Angela et al.,"Yeast SNF1 Is Functionally Related to Mammalian AMP-activated Protein Kinase and Regulates Acetyl-CoA Carboxylase in Vivo", The Journal of Biological Chemistry, vol. 269, No. 30, Jul. 29, 1994, pp. 19509-19515.

\* cited by examiner

US 10,066,245 B2

MICROBIAL PRODUCTION OF 3-HYDROXYPROPIONIC ACID

CROSS REFERENCE TO RELATED APPLICATIONS

This application is the National Phase entry of PCT/EP2014/062246, which claims priority to European Patent Application No. 13172149.0, filed Jun. 14, 2013. The content of these applications is incorporated herein by reference in their entirety.

TECHNICAL FIELD

The present invention relates to a recombinant yeast cells and their use in the production of 3-hydroxypropionic acid (3-HP).

BACKGROUND ART

For more than a century, fossil fuels have been the primary feedstock for the chemical industries. However, new discoveries of fossil fuel deposits are diminishing whilst demand for fossil fuel based chemicals are ever increasing, and soon the supply of fossil fuels will be outweighed by the demand. In an attempt to address this issue a large amount of effort has gone into developing novel biotechnological strategies for producing chemical feedstock from renewable sources (e.g. sugars). In 2004 the Department of Energy in the USA identified a list of 12 target feedstock chemicals to be produced through biotechnological routes. 3-hydroxy propionic acid (3-HP) has been chosen as one of the 12 feedstock chemicals as it can serve as a platform for the development of a range of 3-carbon petrochemical intermediates, and in particular it can be dehydrated to form acrylic acid. More than 1 billion kilograms of acrylic acid are produced annually as it is the monomeric building block for polymeric acrylates which can be used in a wide range of consumer products, e.g. personal care products, adhesives, coatings and paints, and the annual total market size is over USD100 billion. One particularly important application of 3-HP is for the production of superabsorbent polymers (SAP), which constitute a significant part of baby diapers and incontinence products. It is evidently desirable to develop a more sustainable way of producing acrylic acid, hence this is why a significant amount of research continues towards the development of a biotechnological method of producing 3-HP, the acrylic acid precursor.

Conventional biological processes for producing 3-HP are performed by a complicated metabolic pathway. Therefore, it is difficult to control the process effectively, resulting in low production yield and productivity. For this reason it is necessary to design a 3-HP production pathway which controls the quantity of biochemical precursors in the cytosol such that the flux towards late stage biochemical intermediates in said 3-HP production pathway is favoured and alternative biological pathways are disfavoured.

EP 2505656 discloses a method of producing 3-HP using a malonic semialdehyde reducing pathway, wherein the process utilises an NADPH dependent malonyl-CoA reductase which may be derived from *C. aurantiacus* and an NADP/NADPH dependent GAPDH variant to resolve a redox imbalance within the metabolic process. The maximum reported yield of 3-HP was approximately 1.3 g/L.

Rathnasingh et al. (J. Biotechnol. 2012) discloses a method of producing 3-HP using *Escherichia coli* cells, wherein said cells overexpress MCR from *C. aurantiacus* and ACC in the malonyl-CoA pathway. The maximum reported yield of 3-HP was 2.14 mmol/L (0.19 g/L).

WO 2008/080124 discloses a method of producing butanol using modified yeast, wherein said method produces increased quantities of cytosolic acetyl-CoA by overexpressing PDC1 and ALD6 which may be derived from *S. cerevisiae* and ACS which may be derived from *S. entherica*. This method does not utilise the malonyl-CoA pathway.

WO 2007/024718 discloses a method of producing isoprenoid compounds using genetically modified host cells, wherein said cells are modified to produce increased levels of acetyl-CoA by increasing ALD and ACS activity. This method does not utilise the malonyl-CoA pathway.

In *S. cerevisiae*, acetyl-CoA carboxylase is tightly regulated at the transcriptional, translational and post-translational levels (Shirra, M. K. et al, 2001; Nielsen, J. 2009). At the level of the protein, Snf1 kinase is the major kinase which phosphorylates and inactivates ACC1 in vivo (Shirra, M. K. et al, 2001). WO 2012/017083 discloses a method of producing wax esters using modified yeast, wherein the quantity of cytosolic acetyl-CoA is increased through increasing the activity of ACC1 by mutating ACC1 at dephosphorylation sites such that it is no longer inactivated by Snf1.

DESCRIPTION OF THE INVENTION

The present invention relates to a recombinant yeast cell which produces high supernatant concentrations (up to 10 g/L) of 3-HP by increasing the flux towards cytosolic malonyl-CoA, which is reduced to 3-HP by malonyl-CoA reductase (MCR). The recombinant yeast cell overexpresses pyruvate decarboxylase (PDC), aldehyde dehydrogenase (ALD), Acetyl-CoA synthase (ACS), and a mutated Acetyl-CoA Carboxylase (ACC*) (the enzyme is mutated at two dephosphorylation sites to prevent inactivation by Snf1) which increases the conversion of pyruvate to malonyl-CoA. MCR derived from *Chloroflexus aurantiacus* reduces malonyl-CoA to 3-HP using NADPH as a cofactor. In order to resolve the resulting redox imbalance within the metabolic process the endogenous NAD dependent glyceraldehyde-3-phosphate dehydrogenase (GAPDH) is replaced with with an NADP dependent GAPDH variant.

None of the above cited art discloses the specific combination of the features of the herein described invention. Furthermore, the recombinant yeast of present invention produces 3-HP in substantially greater yields than the cited art.

In a first aspect the present invention relates to a yeast cell for use in producing 3-hydroxypropionic acid (3-HP), wherein said yeast cell incorporates genetic modification such that said cell expresses the enzymes:
  Pyruvate decarboxylase (PDC)
  Aldehyde dehydrogenase (ALD)
  Acetyl-CoA synthase (ACS)
  Acetyl-CoA carboxylase (ACC*) mutated in at least one dephosphorylation site to prevent inactivation by Snf1
  Malonyl-CoA reductase (MCR), said cell has a reduced level of activity of NAD dependent glyceraldehyde-3-phosphate dehydrogenase (GAPDH), suitably by virtue of deletion, attenuation, disruption, down-regulation, or mutation of one or more genes expressing NAD dependent GAPDH and has at least one exogenous gene encoding NADP dependent GAPDH and/or has up-regulation of at least one endogenous gene expressing NADP dependent GAPDH. It has been found that combined expression of the enzymes NADP dependent GAPDH, PDC, ALD, ACS, ACC* and MCR in said host cell increases metabolic flux towards 3-HP via malonyl-CoA compared to an otherwise similar yeast cell lacking said genetic modification.

In a preferred embodiment of the invention the recombinant yeast strain comprises one or more exogenous nucleic acid molecules encoding at least one of PDC, ALD, ACS, ACC* and/or MCR. Preferably, said nucleic acid molecule is expressed from multiple integrations of said nucleic acid molecule in the host cell genome. Such a multiply integrated nucleic acid molecule may encode, for example, MCR.

The nucleic acid molecule encoding PDC may be derived from *Saccharomyces cerevisiae*. 'Derived from' is used herein to specify the species from which the original genetic material encoding the specified enzyme originated.

The nucleic acid molecule encoding ALD may be derived from *Saccharomyces cerevisiae*.

The nucleic acid molecule encoding ACS may be derived from *Salmonella enterica*.

The ACC* enzyme may be mutated in at least two dephosphorylation positions in the enzyme. In a preferred embodiment, the ACC* enzyme is mutated at amino acid positions Ser659 and Ser1157. Suitably Ser659 and Ser1157 are replaced by amino acids comprising side chains which are incapable of being phosphorylated, preferably Ala, Val, Leu, Ile, Pro, Phe, Trp and/or Met. The nucleic acid molecule encoding the non-mutated version of the ACC* enzyme may be derived from *Saccharomyces cerevisiae*.

The nucleic acid molecule encoding MCR may be derived from *Chloroflexus aurantiacus*.

The nucleic acid molecule encoding NADP dependent GAPDH may be derived from *Clostridium acetobutylicum, Kluyveromyces lactis* or *Bacillus subtilis*.

In another aspect, the present invention relates to a method for producing 3-HP, said method comprising culturing yeast cells as described herein under conditions such that 3-HP is produced.

In a preferred embodiment of the invention, the yeast cells are cultured on a medium comprising at least one carbon substrate, wherein said carbon substrate may be glucose or galactose.

Preferably, culturing said yeast cells on a medium comprising at least one carbon substrate produces a supernatant concentration of at least 5 g/L 3-HP, more preferably said yeast cells produce a supernatant concentration of at least 6 g/L 3-HP, more preferably said yeast cells produce a supernatant concentration of at least 7 g/L 3-HP, more preferably said yeast cells produce a supernatant concentration of at least 8 g/L 3-HP, and most preferably said yeast cells produce a supernatant concentration of at least 9 g/L 3-HP.

In another preferred embodiment of the invention, said method further comprises isolating 3-HP produced by said recombinant yeast strain.

FIGURES

FIG. 1: Bar chart comparing yeast cells transformed with ACC comprising zero, one or two mutations at dephosphorylation sites.

Figure 2:
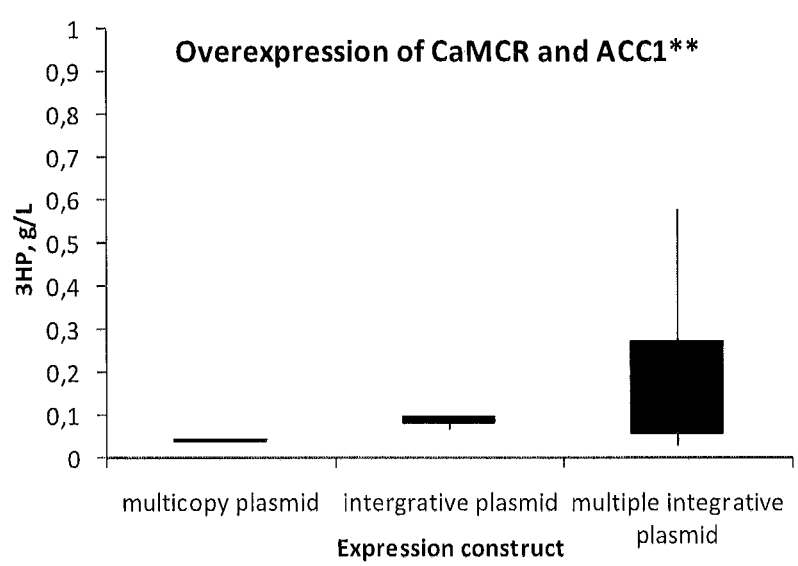

FIG. 2: Bar chart comparing the supernatant concentration of 3-HP produced by yeast cells transformed with a multicopy vector, a single integrative vector and a multiple integrative vector.

Figure 3:
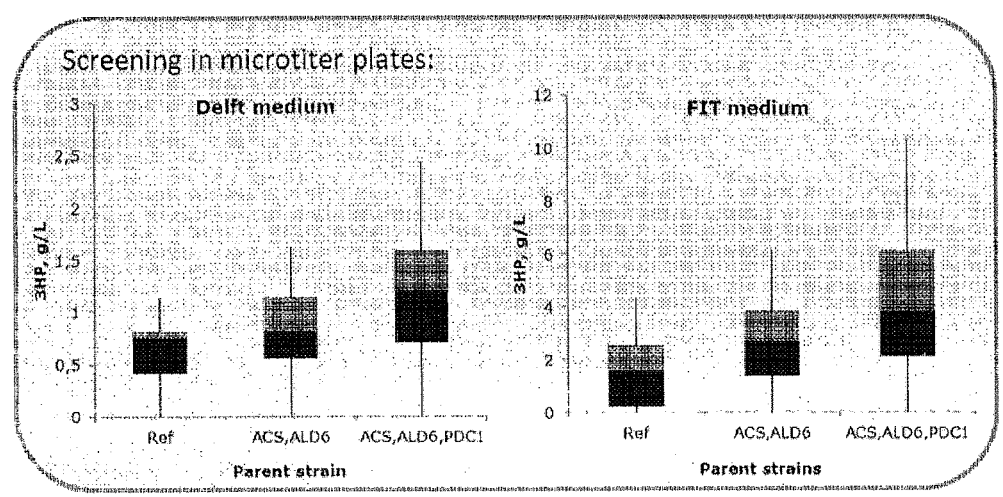

FIG. 3: Bar chart comparing the supernatant concentration of 3-HP produced by yeast cells overexpressing ACS, ALD6 and/or PDC1 in both DELFT and FIT media.

Figure 4:
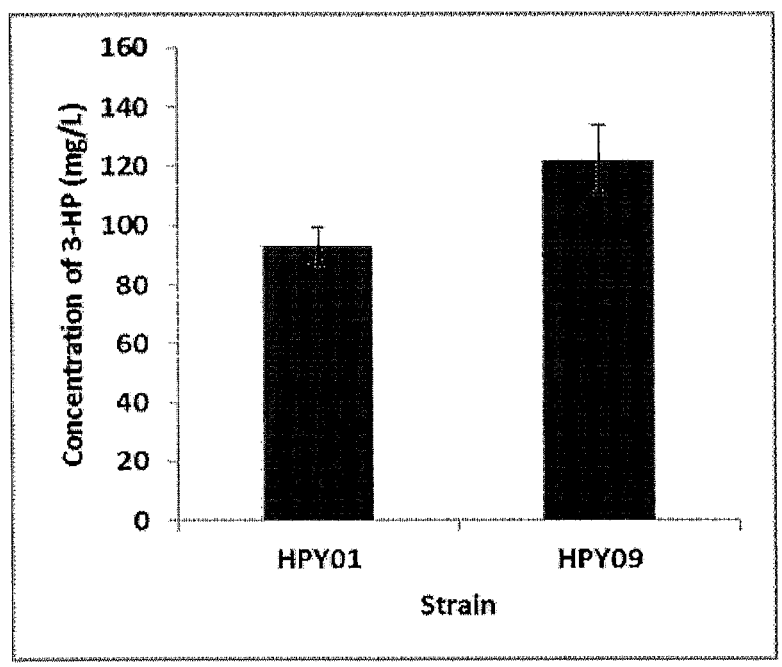

FIG. 4: Bar chart comparing the supernatant concentration of 3-HP produced by yeast cells with increased pool of available NADPH and those with no increased pool of available NADPH.

Figure 5:
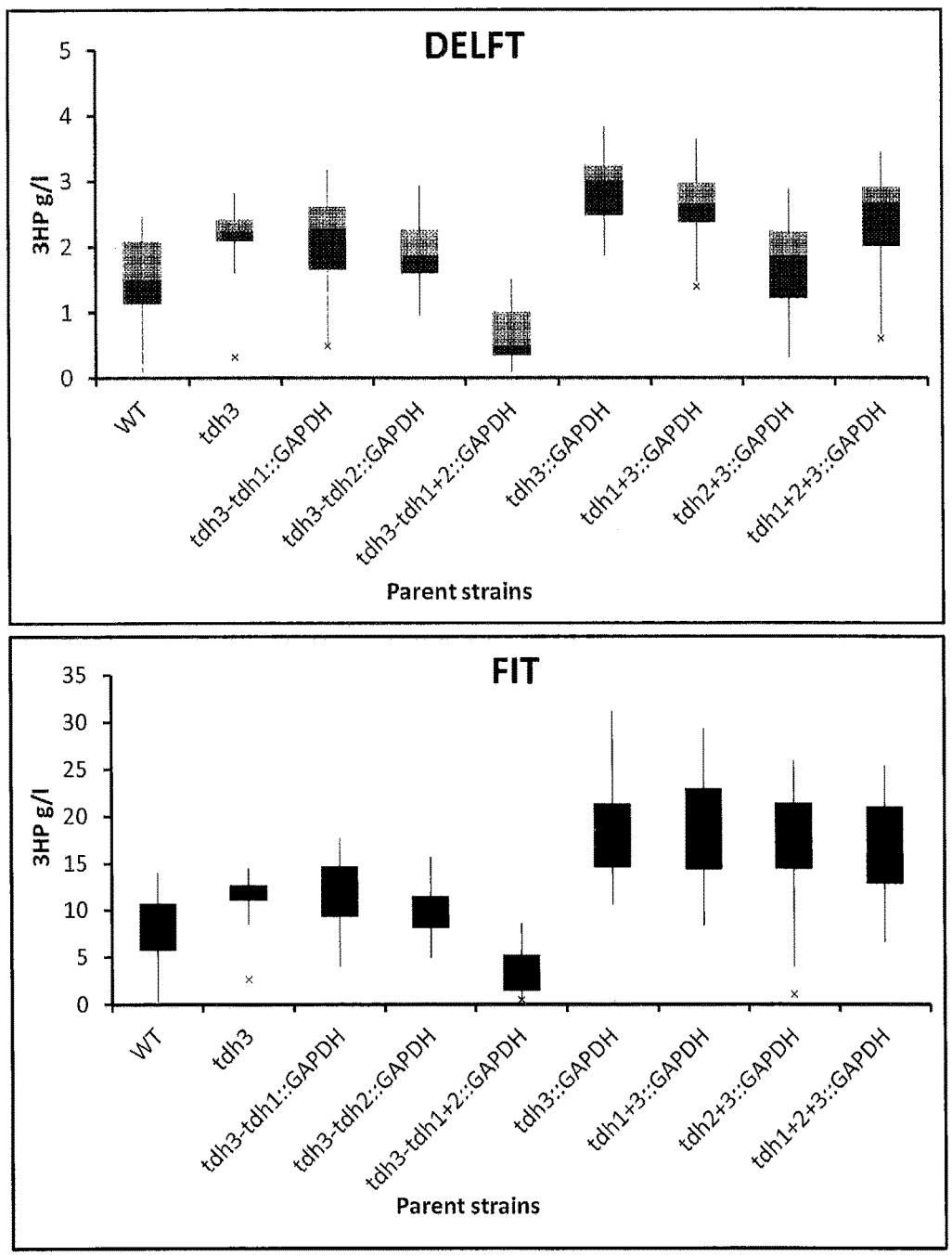

FIG. 5: Bar chart demonstrating the effect of replacing the coding sequence of endogenous NAD dependent GAPDH with NADP dependent GAPDH on supernatant concentration of 3-HP in both DELFT and FIT media.

Figure 6:
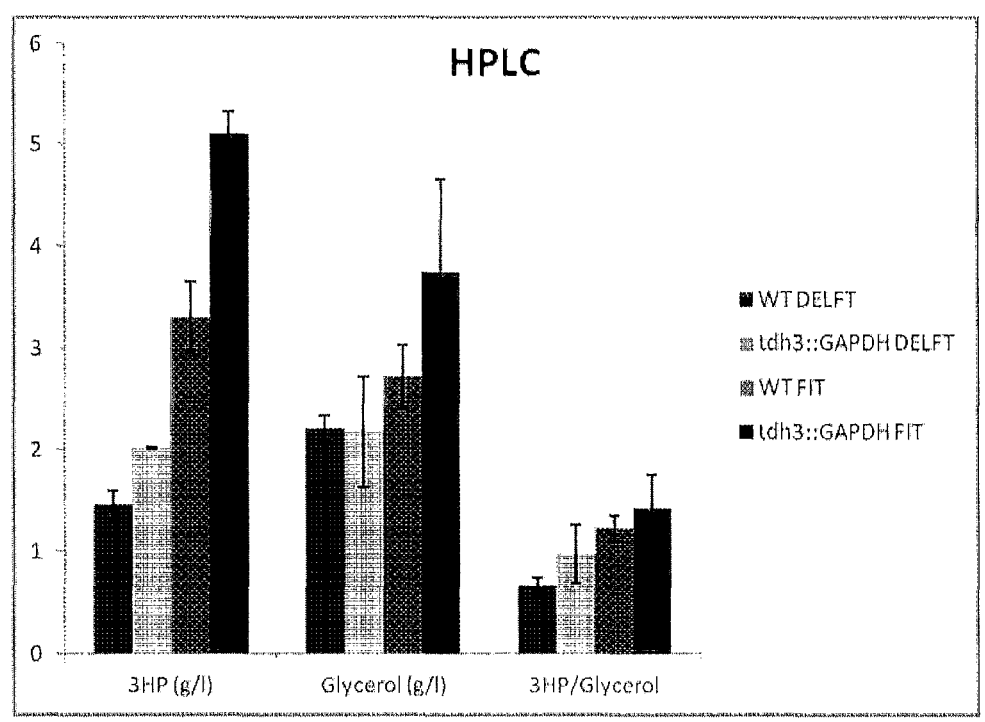

FIG. 6: Bar chart comparing the supernatant concentration of 3-HP produced by yeast cells with improved NADPH supply in DELFT and FIT media.

Figure 7:
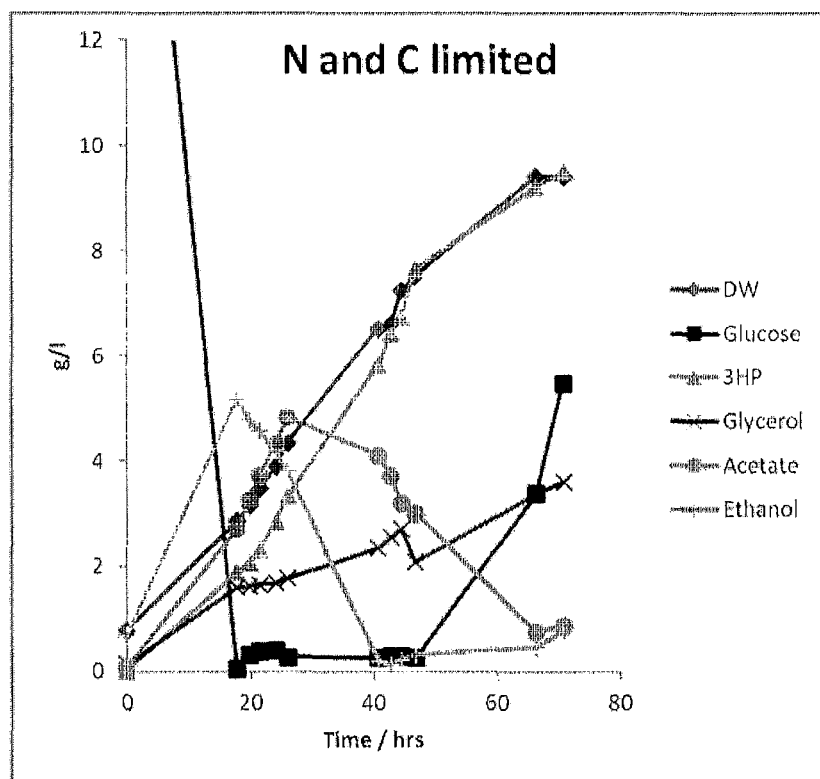

FIG. 7: Graph showing the supernatant concentration of 3-HP, glucose, glycerol, acetate and ethanol vs time in an N and C limited fed batch fermentation of highest producing yeast strain ST687

Figure 8:
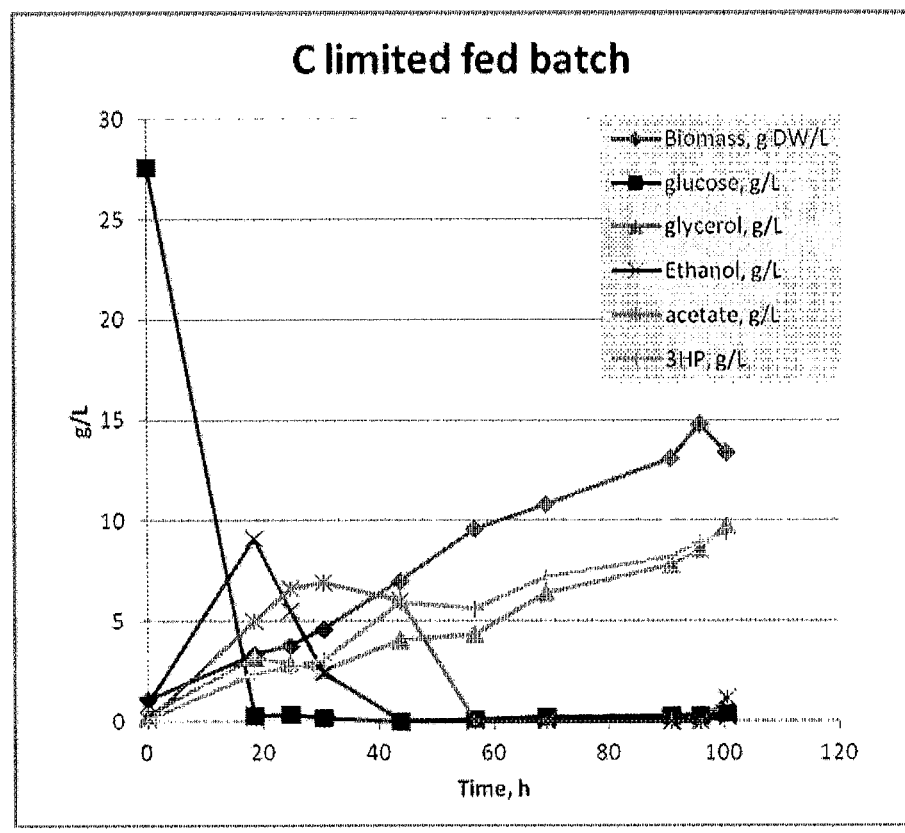

FIG. 8: Graph showing the supernatant concentration of 3-HP, glucose, glycerol, acetate and ethanol vs time in a C limited fed batch fermentation of the highest producing yeast strain ST687

EXAMPLES

TABLE 1

| Oligonucleotide sequences | | |
|---|---|---|
| Oligo name | Oligo sequence 5' --> 3' | Seq ID NO |
| ACC1m_fw | CGTGCGAUTCATTTCAAAGTCTTCAACAATTT | Seq ID NO 11 |
| ACC1m_rv | AGTGCAGGUAAAACAATGAGCGAAGAAAGCTTA | Seq ID NO 12 |
| CaMCR_fw_NEW | ATCTGTCAUAAAACAATGAGTGGTACAGGTAG | Seq ID NO 13 |
| CaMCR_rv_NEW | CACGCGAUTCAGACTGTAATGGCTCTACCTC | Seq ID NO 14 |
| PTEF1_fw | ACCTGCACUTTGTAATTAAAACTTAG | Seq ID NO 15 |
| PPGK1_rv | ATGACAGAUTTGTTTTATATTTGTTG | Seq ID NO 16 |
| ACC1-WT-UP | ATTTGCGGCCGCTTTAGTTTCTACCATGAGCGAAG | Seq ID NO 17 |
| ACC1-WT-DOWN | GGCGAGCTCGCAAGGTTTATTTCAAAGTCTT | Seq ID NO 18 |
| F-1-DOWNz | CATATGACAAATCTGAAACAGCAACAGCCCTGTTCATACC | Seq ID NO 19 |
| F-2-UP | GGTATGAACAGGGCTGTTGCTGTTTCAGATTTGTCATATG | Seq ID NO 20 |

TABLE 1-continued

Oligonucleotide sequences

| Oligo name | Oligo sequence 5' --> 3' | Seq ID NO |
| --- | --- | --- |
| F-3-DOWN | ATGGCAATCAAAAGACCACCATCAGCTAGTTGACGCAGTA | Seq ID NO 21 |
| F-4-UP | TACTGCGTCAACTAGCTGATGGTGGTCTTTTGATTGCCAT | Seq ID NO 22 |
| ACSse_U1_fw | AGTGCAGGUAAAACAATGTCACAAACACAC | Seq ID NO 23 |
| ACSse_U1_rv | CGTGCGAUTCATGATGGCATAGCAATAG | Seq ID NO 24 |
| ald6_U2_fw | ATCTGTCAUAAAACAATGACTAAGCTACACTTTGACAC | Seq ID NO 25 |
| ald6_U2_rv | CACGCGAUTCACAACTTAATTCTGACAGCTTTTAC | Seq ID NO 26 |
| pdc1_U1longer_fw | AGTGCAGGUAAAACAATGTCTGAAATTACTTTGGGTAAATATTTG | Seq ID NO 27 |
| pdc1_U1longer_rv | CGTGCGAUTCATTGCTTAGCGTTGGTAGCAGCAGTC | Seq ID NO 28 |
| PTEF1_rv | CACGCGAUGCACACACCATAGCTTC | Seq ID NO 29 |

TABLE 2

Primers and templates used to generate gene fragments for USER cloning and yeast transformation by PCR

| Fragment name | Gene | Fw_primer | Rv_primer | Template DNA |
| --- | --- | --- | --- | --- |
| ACC**<- | ACC1$^{Ser659Ala, Ser1157Ala}$ from S. cerevisiae | ACC1m_fw | ACC1m_rv | pAD |
| ->CaMCR | Malonyl-CoA reductase from Chloroflexus aurantiacus | CaMCR_fw_NEW | CaMCR_rv_NEW | pYC6 |
| <-ScPTEF1-ScPPGK1-> | Fused promoters of tef1 and pgk1 genes from S. cerevisiae | PTEF1_fw | PPGK1_rv | plasmid pSP-GM1 |
| ACC-pTEFpPGK-CaMCR | ACC1**<-ScPTEF1-ScPPGK1->CaMCR | ACC1m_fw | CaMCR_rv_NEW | P298 |
| ACSse<- | Acetyl-CoA synthetase from Salmonella enterica | ACSse_U1_fw | ACSse_U1_rv | P324 |
| ScALD6-> | Acetaldehyde dehydrogenase 6 from S. cerevisiae | ald6_U2_fw | ald6_U2_rv | S. cerevisiae gDNA |
| ScPDC1<- | Pyruvate decarboxylase isozyme 1 from S. cerevisiae | pdc1_U1longer_fw | pdc1_U1longer_rv | S. cerevisiae gDNA |
| <-ScPTEF1 | TEF1 promoter from S. cerevisiae | PTEF1_fw | PTEF1_rv | S. cerevisiae gDNA |

TABLE 3

Plasmids

| Plasmid name | Parent plasmid | Selection marker | Gene 1 | Promoter | Gene 2 |
| --- | --- | --- | --- | --- | --- |
| P298 | p054 pESC-URA-USER | URA3 | ACC1**<- (Seq ID NO 1) | <-ScPTEF1-ScPPGK1-> (Seq ID NO 3) | ->CaMCR (Seq ID NO 2) |
| P343 | P0255 pX-2-loxP-KlURA3 | KlURA3 | ACC1**<- (Seq ID NO 1) | <-ScPTEF1-ScPPGK1-> (Seq ID NO 3) | ->CaMCR (Seq ID NO 2) |
| P376 | P322 | KlURA3 | ACC1**<- (Seq ID NO 1) | <-ScPTEF1-ScPPGK1-> (Seq ID NO 3) | ->CaMCR (Seq ID NO 2) |
| P474 | P376 | KlURA3 | ACC1**<- (Seq ID NO 1) | <-ScPTEF1-ScPPGK1-> (Seq ID NO 3) | ->CaMCR (Seq ID NO 2) |
| P380 | p257 (pX-3-KlLEU2) | KlLEU2 | ACSse<- (Seq ID NO 4) | <-ScPTEF1-ScPPGK1-> (Seq ID NO 3) | ScALD6-> (Seq ID NO 5) |
| P382 | p258 (pX-4-LoxP-SpHIS5) | SpHIS5 | ScPDC1<- (Seq ID NO 6) | <-ScPTEF1 (Seq ID NO 7) | |

TABLE 4

Yeast strains

| Strain | Parent strain | Genotype |
| --- | --- | --- |
| CEN.PK102-5B | | mata, ura3, his3, leu2 |
| CEN.PK102-5D | | mata, ura3 |
| tdh3-null | CEN.PK102-5B | mata, ura3, his3, leu2, tdh3::LoxP |
| tdh1::CaGAPDH, tdh3 | tdh3-null | mata, ura3, his3, leu2, tdh1::CaGAPDH-LoxP, tdh3::LoxP |
| tdh2::CaGAPDH, tdh3 | tdh3-null | mata, ura3, his3, leu2, tdh2::CaGAPDH-LoxP, tdh3::LoxP |
| tdh1 + 2::CaGAPDH, tdh3 | tdh2::CaGAPDH, tdh3 | mata, ura3, his3, leu2, tdh1::CaGAPDH-LoxP, tdh2::CaGAPDH-LoxP, tdh3::LoxP |
| tdh3::CaGAPDH | CEN.PK102-5B | mata, ura3, his3, leu2, tdh3::CaGAPDH-LoxP |
| tdh1 + 3::CaGAPDH | tdh3::CaGAPDH | mata, ura3, his3, leu2, tdh1::CaGAPDH-LoxP, tdh3::CaGAPDH-LoxP |
| tdh2 + 3::CaGAPDH | tdh3::CaGAPDH | mata, ura3, his3, leu2, tdh2::CaGAPDH-LoxP, tdh3::CaGAPDH-LoxP |
| tdh1 + 2 + 3::CaGAPDH | tdh2 + 3::CaGAPDH | mata, ura3, his3, leu2, tdh1::CaGAPDH-LoxP, tdh2::CaGAPDH-LoxP, tdh3::CaGAPDH-LoxP |

Example 1. Cloning of Over-Expression Targets into Expression Plasmids

All plasmids listed in table 3 were generated by USER cloning using PCR generated gene fragments, which were amplified according to table 2. The typical USER reaction was as follows: 1 µl of linearized and nicked parent plasmid was mixed with 1 µl of promoter fragment, 2 µl of gene fragment, 0.5 µl Taq polymerase buffer, 0.5 µl USER enzyme (NEB). The mix was incubated at 37° C. for 25 min, at 25° C. for 25 min and transformed into chemically competent E. coli DH5alpha. The clones with correct inserts were identified by colony PCR and the plasmids were isolated from overnight E. coli cultures and confirmed by sequencing.

The expression plasmids were transformed into S. cerevisiae cells using the lithium acetate transformation protocol. The cells were selected on synthetic complete (SC) agar medium without uracil, histidine and leucine.

Example 2. ACC1** Engineering Acetyl-CoA Carboxylase for Improving the Production of 3-Hydroxypropionic Acid Ser659 and Ser1157 of ACC1 were identified as two putative phosphorylation sites according to the phosphorylation recognition motif (Hyd-X-Arg-XX-Ser-XXX-Hyd) for yeast Snf1 (Dale, S. et al, 1995). One of which, Ser1157 was verified by a phosphoproteome study (Ficarro, S. et al, 2002). Ser659 has not been reported through experimental data so far. Therefore, we have constructed mutated ACC1 with either one or two assumed phosphorylation sites.

The endogenous ACC1 gene (wild-type) encoding acetyl-CoA carboxylase was amplified from genomic DNA of CEN.PK.113-5D by PCR with Phusion high-fidelity polymerase. The primers are listed in Table 1. The single mutatation $ACC1^{Ser1157Ala}$ and double mutation $ACC1^{Ser659Ala,\ Ser1157Ala}$ were introduced by oligonucleotide primers. Three versions of ACC1 were digested with NotI and SacI, and then ligated into the corresponding sites of pSP-GM2 (Chen et al., 2012), resulting in plasmid pAW (containing wild-type ACC1), pAS (containing single mutated ACC1) and pAD (containing double mutated ACC1), respectively.

For re-constructing the pathway for 3-HP production, the gene CaMCR encoding malonyl-CoA reductase from Chloroflexus aurantiacus was codon optimized for expression in yeast and synthesized by GenScript (Piscataway, N.J., USA). CaMCR was cloned into pIYC04 (Chen et al., 2013) using the BamHI and XhoI cloning sites downstream of the TEF1 promoter, resulting in plasmid pYC6. To evaluate the effect of engineered ACC1 on 3-HP production, plasmids combinations pSP-GM2/pYC6, pAW/pYC6, pAS/pYC6 and pAD/pYC6 were transformed into CEN.PK 113-11C to construct yeast recombinant strain HPY15 to HPY18, respectively.

For the cultivation of yeast recombinant strains, 20 ml cultures in 100 ml unbaffled cotton-stopped flasks were inoculated with an amount of pre-culture that resulted in a final optical density of 0.02 at 600 nm (OD600). The strains were grown at 30° C. with 180 r.p.m. orbital shaking in defined minimal medium with 20 g l$^{-1}$ glucose as described before (Chen et al., 2013). Samples were taken periodically to measure the cell mass, concentration of 3-HP, residual glucose and other metabolites.

The results are shown in FIG. 1. Overexpression of wild-type ACC1 HPY16 increased 3-HP production by 60%, compared to the reference strain HPY15. Overexpression of mutated ACC1 by blocking the phosphorylation sites, HPY17 and HPY18, further enhanced the production of 3-HP. Double mutated $ACC1^{Ser659Ala,\ Ser1157Ala}$ HPY18 gave the highest improvement, around three-fold, relevant to that of the reference strain.

Example 3. Production of 3HP in S. cerevisiae by Over-Expression of CaMCR and ACC1 from Multiple Integration Plasmids CEN.PK102-5D was transformed with either episomal multicopy plasmid p298, or single integrative plasmid p343, or multiple integration plasmid p376. All three plasmids tested harboured ACC1 and CaMCR. Four single transformants for each plasmid tested were inoculated in 0.5 ml SC ura- in a 96-deep well microtiter plate with air-penetrable lid (EnzyScreen). The plates were incubated at 30° C. with 250 rpm agitation at 5 cm orbit cast overnight. 50 µl of the overnight cultures were used to inoculate 0.5 ml Delft medium (Delft medium described in WO 2011/147818) in a 96-deep well plate and 0.5 ml FIT Fed-batch-media (M2P labs). Fermentation was carried out for 72 hours at the same conditions as above.

At the end of the cultivation the $OD_{600}$ was measured. 10 µl of the sample was mixed with 190 µl water and absorbance was measured at 600 nm wave length in a spectrophotometer (BioTek).

The culture broth was spun down and the supernatant analyzed for 3-hydroxypropionic acid concentration using enzymatic assay, which was performed as follows: 20 µl of standards (3HP at concentrations from 0.03 to 1 g/L in Delft medium) and samples were added to a 96-well flat bottom transparent plate (Greiner). 180 µl of mix (14.8 ml water, 2 ml buffer (1 mM Tris, 25 mM $MgCl_2$, pH 8.8), 1 ml NADP+ solution (50 mg/ml), and 0.2 ml purified YdfG enzyme in PBS buffer (1500 µg/ml)) was added per well using a multichannel pipette. The start absorbance at 340 nm was measured and the plate was sealed and incubated at 30° C. for 1.5 hours. After incubation the absorbance at 340 nm was measured again. The difference between the end and the start values corrected for the background were in linear correlation with 3HP concentrations. The concentration of 3HP in each sample was calculated from the standard curve.

Expression of ACC1** and CaMCR from the multiple integration plasmid p376 led to a 5 times improvement of 3HP production in the best clone, when compared to a *S. cerevisiae* strain bearing a single integrative vector with the same genes (FIG. 2).

Example 4. Improving 3HP Production in *S. cerevisiae* by Increasing the Precursor Supply Towards Acetyl-CoA Strains harbouring either p380-ALD6-ACS or p380-ALD6-ACS in combination with p382-PDC1 were transformed with p474-CaMCR-ACC1. A minimum of 6 clones were picked, fermented and tested for 3HP production by enzymatic assay as in example 2 (FIG. 3). The best producer of strains having p380-ALD6-ACS in combination with p474-CaMCR-ACC1 gave up to 1.5 fold higher 3HP titer than the wild type (WT) strain with p474-CaMCR-ACC1**, and strains with all three plasmids combined gave up to 2.5 times more than the WT background in both DELFT and FIT media.

Example 5. Effect of Increasing the Pool of Available NADPH on the Production of 3-Hydroxypropionic Acid The effect of increasing NADPH supply on the production of 3-hydroxypropionic acid was tested. The gapN gene from *Streptococcus* mutants, which encodes non-phosphorylating NADP-dependent glyceraldehyde-3-phosphate dehydrogenase, was codon optimized and synthesized by GeneScript (Piscataway, N.J., USA). The gene gapN was cloned into pIYCO4 (Chen et al., 2013) using the restriction sites NotI and SacI, resulting in plasmid pJC2. Plasmids pJC2 and pYC1 were transformed into CEN.PK 113-11C, forming the recombinant yeast strain HPY09. It was found that the over-expression of gapN alone resulted in a final titer of 122 mg l$^{-1}$ 3-HP, which is a 30% improvement compared to the reference strain (FIG. 4).

Example 6. Construction of Strain with Improved NADPH Supply

An elevated level of NADPH was achieved by overexpression of an NADP dependent glyceraldehyde-3-phosphate dehydrogenase gene from either *Clostridium acetobutylicum*, CaGAPDH (Seq ID NO 08), *Kluyveromyces lactis*, KlGAPDH (Seq ID NO 9), or *Bacillus subtilis*, BsGapB (Seq ID NO 10). The NADP dependent GAPDH was expressed in yeast strains, where one, two or three of the endogenous NAD dependent glyceraldehyde-3-phosphate dehydrogenase genes TDH1-3 were deleted and/or exchanged with the CDS of GAPDH. By exchanging the CDS we aimed to ensure that the introduced GAPDH had the same expression profile as the endogenous NAD dependent GAPDH. Additionally, any potential futile cycling between the endogenous GAPDH and the introduced GAPDH was avoided by removing or lowering the level of endogenous GAPDH activity. Eight different combinations were made according to Table 4. Each of those eight strains and a WT strain were all transformed with p380-ALD6-ACS in combination with p382-PDC1 and p474-CaMCR-ACC1**. A minimum of 12 clones for each strain were tested for 3HP production as in example 2 (FIG. 5). In both media tested, there was a significant increase in 3HP yield for the strains where TDH3 was replaced with CaGAPDH. However, there was no further effect when this exchange was combined with any of the other CDS exchanges. The three best producers for the WT and the tdh3::CaGAPDH strains were analyzed further by HPLC (FIG. 6). The 'WT' strains gave 1.46±0.14 g/l and 3.31±0.34 g/l 3HP in DELFT and FIT, respectively. The 'tdh3::CaGAPDH' strains gave 2.01±0.01 g/l and 5.10±0.22 g/l 3HP in DELFT and FIT, respectively. Furthermore, the ratio between 3HP formed and glycerol formed was higher for the tdh3::CaGAPDH strains in both media tested.

The best producer among the tdh3::CaGAPDH strains was named ST687 and was used in future fermentation experiments.

Example 7. Fermentations of High Producing Strain (ST687)

Strain ST687 was fermented under two different fermentation regimes; 1, N and C limited fed batch, and 2, C limited fed batch.

| | N and C limited fed batch | C limited fed batch |
|---|---|---|
| Parameter | Value | Value |
| Reactor number | A1, A3, B2 | A1, A2, A3 |
| Organism | *S. cerevisiae* | *S. cerevisiae* |
| Strain | ST687 | ST687 |
| Batch medium | Mix per reactor: 20 ml (NH$_4$)$_2$SO$_4$ (100 g/L), 25 ml KH$_2$PO$_4$ (120 g/L), 10 ml MgSO$_4$, 7H$_2$O (50 g/L), 1 ml trace metals, 0.2 ml antifoam, add water to 500 ml. Separately autoclave 110 g dextrose in 500 ml water, add 100 ml of this glucose solution to reactor after autoclavation. Also add 1 ml vitamins. | Mix per reactor: 75 ml (NH$_4$)$_2$SO$_4$ (100 g/L), 25 ml KH$_2$PO$_4$ (120 g/L), 10 ml MgSO$_4$, 7H$_2$O (50 g/L), 2 ml trace metals, 0.2 ml antifoam, add water to 500 ml. Separately autoclave 110 g dextrose in 500 ml water, add 40 ml of this glucose solution to reactor after autoclavation. Also add 1 ml vitamins. |
| Feed medium | Mix per feed bottle: 0.5 L of 200 g/L glucose solution. Add about 100 ml (20 g) before inoculation to start the batch phase, then add the rest during the fed-batch phase. | Mix per feed bottle: 225 ml (NH$_4$)$_2$SO$_4$ (100 g/L), 75 ml KH$_2$PO$_4$ (120 g/L), 30 ml MgSO$_4$, 7H$_2$O (50 g/L), 6 ml trace metals, 0.3 ml antifoam. This will make a total of 336 ml. Add the remaining glucose solution (160 ml) to the feed bottle after autoclavation. Also add 3 ml vitamins. |
| Temperature | 30° C. | 30° C. |
| pH | 5 | 5 |
| pH control | with 2M NaOH | with 2M NaOH |
| DO | not controlled | controlled at >20% by stirring speed and aeration |
| Working volume | batch with 0.5 L, then fill up to 1 L during fed-batch | batch with 0.5 L, then fill up to 1 L during fed-batch |
| Agitation | 800 rpm | 800 rpm (variable in the fed-batch phase) |
| Aeration | 1 vvm (1 L/min) | 1 vvm (1 L/min) (variable in the fed-batch phase) |

-continued

|  | N and C limited fed batch | C limited fed batch |
| --- | --- | --- |
| Aeration gas | Air | Air |
| Fermentation lengh | 70 hours | 120 hours |
| Sampling frequency | 2-3 times a day | 2 times a day |

The inoculum was prepared as follows. A stock tube of ST/687 was inoculated into 50 ml SC-ura-his-leu and grown overnight at 30° C. 400 ml fresh medium is added and divided into 3 flasks, 150 ml in each and grown overnight at 30° C. The cultures from overnight shake flasks is combined to obtain a total of about 450 ml, which then is poured into 6×50 ml Falcon tubes. Tubes are spun 4,000×g for 2 min and supernatant is discarded. The rest of the overnight culture is added to the 6 tubes (about 25 ml/tube), resuspended, and pooled into 2 tubes into one to end up with 3 tubes. Inoculate 1 tube per reactor.

Each sample was analyzed by HPLC as in example 4. The results are summarized in table below and in FIGS. 7 and 8.

|  | N and C limited | C limited |
| --- | --- | --- |
| Titers (3-HP) | 9.5 g/L | 9.83 ± 0.43 g/L |
| Prod. Rate in fed batch phase | 0.20 g/L/h | 0.09 ± 0.01 g/L/h |
| Specific yield, g/g DW | 1.01 g/g DW | 0.69 ± 0.05 g/g DW |
| Overall yield, % C-mol/ C-mol glucose | 18% | 13 ± 1% |

Both fermentations involving the best 3-HP producing yeast strain ST687 produced supernatant concentrations of >9 g/L 3-HP. This is a significant increase over the supernatant concentrations disclosed in the prior art.

REFERENCES

Chen, Y., Partow, S., Scalcinati, G., Siewers, V., Nielsen, J. Enhancing the copy number of episomal plasmids in *Saccharomyces cerevisiae* for improved protein production. FEMS Yeast Res. 12, 598-607 (2012).

Chen, Y., Daviet, L., Schalk, M., Siewers, V., Nielsen, J. Establishing a platform cell factory through engineering of yeast acetyl-CoA metabolism. Metab Eng. 15, 48-54 (2013).

Dale, S., Wilson, W. A., Edelman, A. M. & Hardie, D. G. Similar substrate recognition motifs for mammalian AMP-activated protein kinase, higher plant HMG-CoA reductase kinase-A, yeast SNF1, and mammalian calmodulin-dependent protein kinase I. FEBS Letters 361, 191-195 (1995).

Ficarro, S. et al. Phosphoproteome analysis by mass spectrometry and its application to *Saccharomyces cerevisiae*. Nat Biotechnol 20, 301-305 (2002).

Nielsen, J. Systems biology of lipid metabolism: From yeast to human. FEBS Letters 583, 3905-3913 (2009).

Rathnasingh, C., Raj, S. M., Lee, Y., Catherine, C., Ashok, S., Park, S., J. Production of 3-hydroxypropionic acid via malonyl-CoA pathway using recombinant *Escherichia coli* strains. J. Biotechnol., 633-640 (2012).

Shirra, M. K. et al. Inhibition of Acetyl Coenzyme A Carboxylase Activity Restores Expression of the INO1 Gene in a snf1 Mutant Strain of *Saccharomyces cerevisiae*. Mol. Cell. Biol. 21, 5710-5722 (2001).

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention may be summarised according to the following clauses:

1. A yeast cell for use in producing 3-hydroxypropionic acid (3-HP), wherein said yeast cell incorporates genetic modification such that said cell expresses the enzymes:
   Pyruvate decarboxylase (PDC)
   Aldehyde dehydrogenase (ALD)
   Acetyl-CoA synthase (ACS)
   Acetyl-CoA carboxylase (ACC*) mutated in at least one dephosphorylation site to prevent inactivation by Snf1
   Malonyl-CoA reductase (MCR),
   said cell has a reduced level of activity of NAD dependent glyceraldehyde-3-phosphate dehydrogenase (GAPDH) by virtue of deletion, attenuation, disruption, down-regulation, or mutation of one or more genes expressing NAD dependent GAPDH and has at least one exogenous gene encoding NADP dependent GAPDH and/or has up-regulation of at least one endogenous gene expressing NADP dependent GAPDH, and
   wherein combined expression of the enzymes NADP dependent GAPDH, PDC, ALD, ACS, ACC* and MCR in said host cell increases metabolic flux towards 3-HP via malonyl-CoA compared to an otherwise similar yeast cell lacking said genetic modification.

2. A yeast cell as defined in clause 1, comprising one or more exogenous nucleic acid molecules encoding at least one of PDC, ALD, ACS, ACC* and/or MCR.

3. A yeast cell as defined in clause 2, wherein a said nucleic acid molecule is expressed from multiple integrations of said nucleic acid molecule in the host cell genome.

4. A yeast cell as defined in clause 2, wherein a nucleic acid molecule encoding PDC is derived from *Saccharomyces cerevisiae*.

5. A yeast cell as defined in clause 2, wherein the nucleic acid molecule encoding ALD is derived from *Saccharomyces cerevisiae*.

6. A yeast cell as defined in clause 2, wherein a nucleic acid molecule encoding ACS is derived from *Salmonella entherica*.

7. A yeast cell as defined in clause 2, wherein a ACC* enzyme is mutated in at least two dephosphorylation positions in the enzyme.

8. A yeast cell as defined in clause 7, wherein the ACC* enzyme is mutated at amino acid positions Ser659 and Ser1157, wherein Ser659 and Ser1157 are replaced by amino acids comprising side chains which are incapable of being phosphorylated.

9. A yeast cell as defined in clause 8, wherein said amino acids comprising side chains which are incapable of being phosphorylated are Ala, Val, Leu, Ile, Pro, Phe, Trp, Met.

10. A yeast cell as defined in clause 8, wherein the nucleic acid molecule encoding the non-mutated version of the ACC* enzyme is derived from *Saccharomyces cerevisiae*.

11. A yeast cell as defined in clause 2, wherein a nucleic acid molecule encoding MCR is derived from *Chloroflexus aurantiacus*.

12. A yeast cell as defined in clause 1, wherein a nucleic acid molecule encoding NADP dependent GAPDH is derived from *Clostridium acetobutylicum, Kluyveromyces lactis* or *Bacillus subtilis*.

13. A method for producing 3-HP, said method comprising culturing yeast cells as claimed in any of the preceding claims under conditions such that 3-HP is produced.

14. A method as defined in clause 13, wherein said yeast cells are cultured on a medium comprising at least one carbon substrate.

15. A method as defined in clause 14, wherein said carbon substrate is glucose, xylose, arabinose, or galactose.

16. A method as defined in clause 13, wherein said yeast cells produce a supernatant concentration of at least 5 g/L 3-HP.

17. A method as defined in clause 13, wherein said yeast cells produce a supernatant concentration of at least 6 g/L 3-HP.

18. A method as defined in clause 13, wherein said yeast cells produce a supernatant concentration of at least 7 g/L 3-HP.

19. A method as defined in clause 13, wherein said yeast cells produce a supernatant concentration of at least 8 g/L 3-HP.

20. A method as defined in clause 13, wherein said yeast cells produce a supernatant concentration of at least 9 g/L 3-HP. n 21. A method as defined in clause 13, wherein said method further comprises isolating 3-HP produced by said yeast cells.

---

The invention claimed is:

1. A genetically modified yeast cell for use in producing 3-hydroxypropionic acid (3-HP), wherein said yeast cell expresses the enzymes:
Pyruvate decarboxylase (PDC),
Aldehyde dehydrogenase (ALD),
Acetyl-CoA synthase (ACS),
Acetyl-CoA carboxylase (ACC*), wherein the ACC* is yeast acetyl-CoA carboxylase mutated in at least one phosphorylation site to prevent inactivation by yeast sucrose non-fermenting 1 (Snf1), and
Malonyl-CoA reductase (MCR),
wherein the yeast cell has a reduced level of activity of NAD-dependent glyceraldehyde-3-phosphate dehydrogenase (GAPDH) by deletion or disruption of one or more genes encoding a NAD-dependent GAPDH,
wherein the yeast cell has been transformed with at least one exogenous nucleic acid molecule encoding a NADP-dependent GAPDH, and
wherein culturing said yeast cell expressing the enzymes NADP-dependent GAPDH, PDC, ALD, ACS, ACC* and MCR on a medium comprising at least one carbon substrate produces a supernatant concentration of at least 9 g/L 3-HP.

2. The yeast cell of claim 1, comprising one or more exogenous nucleic acid molecules encoding at least one of the enzymes PDC, ALD, ACS, ACC* and/or MCR.

3. The yeast cell of claim 2, wherein said one or more exogenous nucleic acid molecules is expressed from multiple integrations of said one or more exogenous nucleic acid molecules in the yeast cell genome.

4. The yeast cell of claim 2, wherein the nucleic acid molecule encoding the PDC enzyme is derived from *Saccharomyces cerevisiae*.

5. The yeast cell of claim 2, wherein the nucleic acid molecule encoding the ALD enzyme is derived from *Saccharomyces cerevisiae*.

6. The yeast cell of claim 2, wherein the nucleic acid molecule encoding the ACS enzyme is derived from *Salmonella entherica*.

7. The yeast cell of claim 2, wherein the ACC* enzyme is mutated in at least two phosphorylation sites in the enzyme.

8. The yeast cell of claim 2, wherein the nucleic acid molecule encoding the non-mutated version of the ACC* enzyme is derived from *Saccharomyces cerevisiae*.

9. The yeast cell of claim 8, wherein the ACC* enzyme is mutated at amino acid positions Ser659 and Ser1157, wherein Ser659 and Ser1157 are replaced by amino acids comprising side chains which are incapable of being phosphorylated.

10. The yeast cell of claim 2, wherein the nucleic acid molecule encoding the MCR enzyme is derived from Chloroflexus *aurantiacus*.

11. The yeast cell of claim 1, wherein the nucleic acid molecule encoding the NADP-dependent GAPDH is derived from *Clostridium acetobutylicum, Kluyveromyces lactis* or *Bacillus subtilis*.

12. A method for producing 3-HP, said method comprising culturing the yeast cell of claim 1 under conditions such that 3-HP is produced.

13. The method of claim 12, wherein said yeast cell is cultured on a medium comprising at least one carbon substrate.

14. The method of claim 12, wherein said method further comprises isolating the 3-HP produced by said yeast cell.

\* \* \* \* \*

SEQUENCE LISTING

<160> NUMBER OF SEQ ID NOS: 29

<210> SEQ ID NO 1
<211> LENGTH: 6702
<212> TYPE: DNA
<213> ORGANISM: Saccharomyces cerevisiae
<220> FEATURE:
<221> NAME/KEY: source
<222> LOCATION: 1..6702
<223> OTHER INFORMATION: /mol_type="unassigned DNA"
       /organism="Saccharomyces cerevisiae"

<400> SEQUENCE: 1

```
atgagcgaag aaagcttatt cgagtcttct ccacagaaga tggagtacga aattacaaac      60
tactcagaaa gacatacaga acttccaggt catttcattg gcctcaatac agtagataaa     120
ctagaggagt ccccgttaag ggactttgtt aagagtcacg gtggtcacac ggtcatatcc     180
aagatcctga tagcaaataa tggtattgcc gccgtgaaag aaattagatc cgtcagaaaa     240
tgggcatacg agacgttcgg cgatgacaga accgtccaat tcgtcgccat ggccacccca     300
gaagatctgg aggccaacgc agaatatatc cgtatggccg atcaatacat tgaagtgcca     360
ggtggtacta ataataacaa ctacgctaac gtagacttga tcgtagacat cgccgaaaga     420
gcagacgtag acgccgtatg ggctggctgg ggtcacgcct ccgagaatcc actattgcct     480
gaaaaattgt cccagtctaa gaggaaagtc atctttattg ggcctccagg taacgccatg     540
aggtctttag gtgataaaat ctcctctacc attgtcgctc aaagtgctaa agtcccatgt     600
attccatggt ctggtaccgg tgttgacacc gttcacgtgg acgagaaaac cggtctggtc     660
tctgtcgacg atgacatcta tcaaaagggt gttgtacct ctcctgaaga tggtttacaa     720
aaggccaagc gtattggttt tcctgtcatg attaaggcat ccgaaggtgg tggtggtaaa     780
ggtatcagac aagttgaacg tgaagaagat ttcatcgctt tataccacca ggcagccaac     840
gaaattccag gctcccccat tttcatcatg aagttggccg gtagagcgcg tcacttggaa     900
gttcaactgc tagcagatca gtacggtaca aatatttcct tgttcggtag agactgttcc     960
gttcagagac gtcatcaaaa aattatcgaa gaagcaccag ttacaattgc caaggctgaa    1020
acatttcacg agatggaaaa ggctgccgtc agactgggga aactagtcgg ttatgtctct    1080
gccggtaccg tggagtatct atattctcat gatgatgaa aattctactt tttagaattg    1140
aacccaagat tcaagtcga gcatccaaca acggaaatgg tctccggtgt taacttacct    1200
gcagctcaat tacaaatcgc tatgggtatc cctatgcata gaataagtga cattagaact    1260
```

```
ttatatggta tgaatcctca ttctgcctca gaaatcgatt tcgaattcaa aactcaagat    1320
gccaccaaga aacaaagaag acctattcca aagggtcatt gtaccgcttg tcgtatcaca    1380
tcagaagatc caaacgatgg attcaagcca tcgggtggta ctttgcatga actaaacttc    1440
cgttcttcct ctaatgtttg gggttacttc tccgtgggta acaatggtaa tattcactcc    1500
ttttcggact ctcagttcgg ccatattttt gcttttggtg aaaatagaca agcttccagg    1560
aaacacatgg ttgttgccct gaaggaattg tccattaggg gtgatttcag aactactgtg    1620
gaatacttga tcaaactttt ggaaactgaa gatttcgagg ataacactat taccaccggt    1680
tggttggacg atttgattac tcataaaatg accgctgaaa agcctgatcc aactcttgcc    1740
gtcatttgcg gtgccgctac aaaggctttc ttagcatctg aagaagcccg ccacaagtat    1800
atcgaatcct tacaaaaggg acaagttcta tctaaagacc tactgcaaac tatgttccct    1860
gtagatttta tccatgaggg taaaagatac aagttcaccg tagctaaatc cggtaatgac    1920
cgttacacat tatttatcaa tggttctaaa tgtgatatca tactgcgtca actagctgat    1980
ggtggtcttt tgattgccat aggcggtaaa tcgcatacca tctattggaa agaagaagtt    2040
gctgctacaa gattatccgt tgactctatg actactttgt tggaagttga aaacgatcca    2100
acccagttgc gtactccatc ccctggtaaa ttggttaaat tcttggtgga aaatggtgaa    2160
cacattatca agggccaacc atatgcagaa attgaagtta tgaaaatgca aatgcctttg    2220
gtttctcaag aaaatggtat cgtccagtta ttaaagcaac ctggttctac cattgttgca    2280
ggtgatatca tggctattat gactcttgac gatccatcca aggtcaagca cgctctacca    2340
tttgaaggta tgctgccaga ttttggttct ccagttatcg aaggaaccaa acctgcctat    2400
aaattcaagt cattagtgtc tactttggaa acatttgta agggttatga caaccaagtt    2460
attatgaacg cttccttgca acaattgata gaggttttga gaaatccaaa actgccttac    2520
tcagaatgga aactacacat ctctgcttta cattcaagat tgcctgctaa gctagatgaa    2580
caaatggaag agttagttgc acgttctttg agacgtggtg ctgttttccc agctagacaa    2640
ttaagtaaat tgattgatat ggccgtgaag aatcctgaat acaaccccga caaattgctg    2700
ggcgccgtcg tggaaccatt ggcggatatt gctcataagt actctaacgg ttagaagcc    2760 catgaacatt ctatatttgt ccatttcttg gaagaatatt acgaagttga aagttattc    2820 aatggtccaa atgttcgtga ggaaaatatc attctgaaat tgcgtgatga aaaccctaaa    2880
gatctagata aagttgcgct aactgttttg tctcattcga aagtttcagc gaagaataac    2940
ctgatcctag ctatcttgaa acattatcaa ccattgtgca agttatcttc taaagtttct    3000
gccatttcct ctactcctct acaacatatt gttgaactag aatctaaggc taccgctaag    3060
gtcgctctac aagcaagaga aatttttgatt caaggcgctt taccttcggt caaggaaaga    3120
actgaacaaa ttgaacatat cttaaaatcc tctgttgtga aggttgccta tggctcatcc    3180
aatccaaagc gctctgaacc agatttgaat atcttgaagg acttgatcga ttctaattac    3240
gttgtgttcg atgtttact tcaattccta acccatcaag acccagttgt gactgctgca    3300
gctgctcaag tctatattcg tcgtgcttat cgtgcttaca ccataggaga tattagagtt    3360
cacgaaggtg tcagttcc aattgttgaa tggaaattcc aactaccttc agctgcgttc    3420
tccacctttc caactgttaa atctaaaatg ggtatgaaca gggctgttgc tgtttcagat    3480
ttgtcatatg ttgcaaacag tcagtcatct ccgttaagag aaggtatttt gatggctgtg    3540
gatcatttag atgatgttga tgaaatttg tcacaaagtt tggaagttat tcctcgtcac    3600
caatcttctt ctaacggacc tgctcctgat cgttctggta gctccgcatc gttgagtaat    3660
```

-continued

```
gttgctaatg tttgtgttgc ttctacagaa ggtttcgaat ctgaagagga aattttggta    3720
aggttgagag aaattttgga tttgaataag caggaattaa tcaatgcttc tatccgtcgt    3780
atcacattta tgttcggttt taaagatggg tcttatccaa agtattatac ttttaacggt    3840
ccaaattata acgaaaatga aacaattcgt cacattgagc cggctttggc cttccaactg    3900
gaattaggaa gattgtccaa cttcaacatt aaaccaattt tcactgataa tagaaacatc    3960
catgtctacg aagctgttag taagacttct ccattggata agagattctt tacaagaggt    4020
attattagaa cgggtcatat ccgtgatgac atttctattc aagaatatct gacttctgaa    4080
gctaacagat tgatgagtga tatattggat aatttagaag tcaccgacac ttcaaattct    4140
gatttgaatc atatcttcat caacttcatt gcggtgtttg atatctctcc agaagatgtc    4200
gaagccgcct tcgtggggttt cttagaaaga tttggtaaga gattgttgag attgcgtgtt    4260
tcttctgccg aaattagaat catcatcaaa gatcctcaaa caggtgcccc agtaccattg    4320
cgtgccttga tcaataacgt ttctggttat gttatcaaaa cagaaatgta caccgaagtc    4380
aagaacgcaa aaggtgaatg ggtatttaag tctttgggta aacctggatc catgcattta    4440
agacctattg ctactcctta ccctgttaag gaatggttgc aaccaaaacg ttataaggca    4500
cacttgatgg gtaccacata tgtctatgac ttcccagaat tattccgcca agcatcgtca    4560
tcccaatgga aaaatttctc tgcagatgtt aagttaacag atgatttctt tatttccaac    4620
gagttgattg aagatgaaaa cggcgaatta actgaggtgg aaagagaacc tggtgccaac    4680
gctattggta tggttgcctt taagattact gtaaagactc ctgaatatcc aagaggccgt    4740
caatttgttg ttgttgctaa cgatatcaca ttcaagatcg gttcctttgg tccacaagaa    4800
gacgaattct tcaataaggt tactgaatat gctagaaagc gtggtatccc aagaatttac    4860
ttggctgcaa actcaggtgc cagaattggt atggctgaag agattgttcc actatttcaa    4920
gttgcatgga atgatgctgc caatccggac aagggcttcc aatacttata cttaacaagt    4980
gaaggtatgg aaactttaaa gaaatttgac aaagaaaatt ctgttctcac tgaacgtact    5040
gttataaacg gtgaagaaag atttgtcatc aagacaatta ttggttctga agatgggtta    5100
ggtgtcgaat gtctacgtgg atctggttta attgctggtg caacgtcaag ggcttaccac    5160
gatatcttca ctatcacctt agtcacttgt agatccgtcg gtatcggtgc ttatttggtt    5220
cgtttgggtc aaagagctat tcaggtcgaa ggccagccaa ttattttaac tggtgctcct    5280
gcaatcaaca aaatgctggg tagagaagtt tatacttcta acttacaatt gggtggtact    5340
caaatcatgt ataacaacgg tgtttcacat ttgactgctg ttgacgattt agctggtgta    5400
gagaagattg ttgaatggat gtcttatgtt ccagccaagc gtaatatgcc agttcctatc    5460
ttggaaacta aagacacatg ggatagacca gttgatttca ctccaactaa tgatgaaact    5520
tacgatgtaa gatggatgat tgaaggtcgt gagactgaaa gtggatttga atatggtttg    5580
tttgataaag ggtctttctt tgaaactttg tcaggatggg ccaaaggtgt tgtcgttggt    5640
agagcccgtc ttggtggtat tccactgggt gttattggtg ttgaaacaag aactgtcgag    5700
aacttgattc ctgctgatcc agctaatcca aatagtgctg aaacattaat tcaagaacct    5760
ggtcaagttt ggcatccaaa ctccgccttc aagactgctc aagctatcaa tgactttaac    5820
aacggtgaac aattgccaat gatgattttg gccaactgga gaggtttctc tggtggtcaa    5880
cgtgatatgt tcaacgaagt cttgaagtat ggttcgttta ttgttgacgc attggttgat    5940
tacaaacaac caattattat ctatatccca cctaccggtg aactaagagg tggttcatgg    6000
```

```
gttgttgtcg atccaactat caacgctgac caaatggaaa tgtatgccga cgtcaacgct    6060
agagctggtg ttttggaacc acaaggtatg gttggtatca agttccgtag agaaaaattg    6120
ctggacacca tgaacagatt ggatgacaag tacagagaat tgagatctca attatccaac    6180
aagagtttgg ctccagaagt acatcagcaa atatccaagc aattagctga tcgtgagaga    6240
gaactattgc caatttacgg acaaatcagt cttcaatttg ctgatttgca cgataggtct    6300
tcacgtatgg tggccaaggg tgttatttct aaggaactgg aatggaccga ggcacgtcgt    6360
ttcttcttct ggagattgag aagaagattg aacgaagaat atttgattaa aaggttgagc    6420
catcaggtag gcgaagcatc aagattagaa aagatcgcaa gaattagatc gtggtaccct    6480
gcttcagtgg accatgaaga tgataggcaa gtcgcaacat ggattgaaga aaactacaaa    6540
actttggacg ataaactaaa gggttttgaaa ttagagtcat tcgctcaaga cttagctaaa    6600
aagatcagaa gcgaccatga caatgctatt gatggattat ctgaagttat caagatgtta    6660
tctaccgatg ataaagaaaa attgttgaag actttgaaat ga                       6702
```

<210> SEQ ID NO 2
<211> LENGTH: 3663
<212> TYPE: DNA
<213> ORGANISM: Chloroflexus aurantiacus
<220> FEATURE:
<221> NAME/KEY: source
<222> LOCATION: 1..3663
<223> OTHER INFORMATION: /mol_type="unassigned DNA"
      /organism="Chloroflexus aurantiacus"

<400> SEQUENCE: 2

```
atgagtggta caggtagatt agcaggtaaa atagcattga taacaggtgg tgccggtaac      60
ataggttccg aattaacaag aagattttg gcagaaggtg ccaccgttat tatctctggt     120
agaaacagag caaagttaac tgccttggct gaaagaatgc aagcagaagc cggtgtccct     180
gctaagagaa ttgatttgga agttatggat ggttctgacc cagtcgctgt aagagcaggt     240
attgaagcca tagtagctag acatggtcaa atcgatatct tggttaacaa cgcaggttca     300
gctggtgcac aaagaagatt ggctgaaatt cctttaactg aagcagaatt gggtccaggt     360
gccgaagaaa cattacatgc atccattgcc aatttgttgg gtatgggttg gcatttgatg     420
agaatagctg caccacacat gcctgttggt agtgcagtta taacgtctc caccatcttc     480 agtagagctg aatattacgg tagaattcct tatgttactc aaaagccgc tttaaatgca     540 ttgtctcaat tagcagccag agaattaggt gctagaggta ttagagttaa caccatattt     600
ccaggtccta tcgaatcaga tagaattaga actgtcttcc aaagaatgga tcaattaaag     660
ggtagacctg aaggtgacac agctcatcac ttttttaaaca ccatgagatt gtgtagagca     720
aacgatcaag gtgccttgga agaagatttt ccatctgtag gtgacgttgc tgacgctgca     780
gtcttcttag cctccgctga aagtgccgct ttgtcaggtg aaactattga agttacacat     840
ggtatggaat tgccagcctg ctctgaaaca tcattgttag caagaaccga tttgagaact     900
attgacgctt ctggtagaac tacattgatc tgtgctggtg accaaattga agaagtcatg     960
gctttgacag gcatgttaag aacctgcggt tctgaagtaa tcattggttt tagatcagca    1020
gccgctttag ctcaattcga acaagcagtt aatgaatcaa gaagattggc aggtgccgat    1080
tttacaccac ctatagcttt accattagat ccaagagatc cagcaaccat cgatgccgta    1140
ttcgactggg gtgctggtga aaatacaggt ggtatacatg cagccgttat cttaccagct    1200
acctctcacg aaccagcacc ttgtgtcata gaagtagatg acgaaagagt tttgaacttc    1260
```

```
ttagctgatg aaatcacagg taccattgtc atagcttcca gattagcaag atattggcaa      1320
agtcaaagat tgactcctgg tgctagagca agaggtccaa gagtaatctt tttgtctaat      1380
ggtgctgatc aaaacggtaa cgtttacggt agaattcaat cagctgcaat aggtcaatta      1440
atcagagttt ggagacatga agctgaattg gattaccaaa gagcatctgc cgctggtgac      1500
cacgtcttac cacctgtatg ggccaatcaa attgttagat ttgctaacag atccttggaa      1560
ggtttagaat tcgcctgtgc ttggactgct caattgttgc atagtcaaag acacatcaac      1620
gaaatcacat tgaacatacc agccaacatc tccgctacca ctggtgctag atctgcatca      1680
gttggttggg ctgaaagttt gatcggtttg catttgggta aagtcgcatt gatcacaggt      1740
ggttccgccg gtatcggtgg tcaaattggt agattgttag cattaagtgg tgccagagtt      1800
atgttggcag ccagagatag acataagtta gaacaaatgc aagctatgat tcaatcagaa      1860
ttggcagaag ttggttacac tgatgttgaa gacagagtcc acatagctcc aggttgcgat      1920
gtctcttcag aagcccaatt ggctgactta gtagaaagaa cttgtctctg tttcggtaca      1980
gttgattatt tgattaataa cgcaggtata gccggtgtag aagaaatggt tatagatatg      2040
cctgttgaag gttggagaca tacattgttc gcaaatttga tctccaacta cagtttgatg      2100
agaaagttgg ctccattaat gaaaaagcaa ggttccggtt acatattgaa cgtttccagt      2160
tacttcggtg gtgaaaaaga tgctgcaata ccatatccta acagagctga ctacgcagtc      2220
tctaaggcag gtcaaagagc aatggccgaa gtatttgcta gattcttagg tcctgaaatc      2280
caaattaatg ctattgcacc aggtcctgtt gaaggtgaca gattaagagg tactggtgaa      2340
agaccaggtt tgtttgccag aagagctaga ttgatcttgg aaaataagag attgaacgaa      2400
ttacatgccg cttttgattgc agccgctaga acagatgaaa gatctatgca cgaattagta      2460
gaattgttgt tgcctaatga cgttcagcc ttggaacaaa accctgctgc accaactgcc      2520
ttgagagaat tagctagaag attcagatct gaaggtgacc cagccgcttc ttcatccagt      2580
gcattgttga acagatcaat agcagccaag ttattggcta gattacataa cggtggttat      2640
gttttgcctg ctgatatttt tgcaaatttg cctaacccac ctgacccatt tttcacaaga      2700
gcccaaattg atagagaagc tagaaaggtt agagacggta tcatgggcat gttgtacttg      2760
caaagaatgc aaccgaatt tgatgttgcc atggctactg tctattactt agctgacaga      2820
aatgtttccg tgaaactttt tcatcctagt ggtggtttga gatatgaaag aactccaaca      2880
ggtggtgaat tgttcggttt accatctcct gaaagattgg ctgaattagt cggttcaaca      2940
gtatacttaa taggtgaaca tttgaccgaa cacttaaatt tgttggcaag agcctatttg      3000
gaaagatacg gtgcaagaca agttgtcatg attgttgaaa ccgaaactgg tgctgaaaca      3060
atgagaagat tattgcatga tcacgttgaa gctggtagat tgatgaccat tgttgctggt      3120
gaccaaatag aagctgcaat cgaccaagct attactagat atggtagacc aggtcctgta      3180
gtttgtactc ttttagacc attacctaca gttccattgg tcggtagaaa agattctgac      3240
tggtcaacag ttttatcaga agcagaattt gccgaattat gcgaacatca attgactcat      3300
cacttcagag tcgccagaaa gattgctttg tctgatggtg cttcattagc attggtaacc      3360
ccagaaacaa ccgctacttc cactacagaa caattcgctt tggcaaactt catcaagacc      3420
actttgcatg ccttcacagc taccattggt gtagaaagtg aaagaactgc tcaaagaata      3480
ttaatcaacc aagttgattt gacaagaaga gccagagctg aagaacctag agacccacac      3540
gaaagacaac aagaattaga aagattcatt gaagcagtat tgttggttac tgccccattg      3600
ccaccagaag cagacacaag atacgcaggt agaatccaca gaggtagagc cattacagtc      3660
``` tga                                                                   3663

<210> SEQ ID NO 3
<211> LENGTH: 1411
<212> TYPE: DNA
<213> ORGANISM: Saccharomyces cerevisiae
<220> FEATURE:
<221> NAME/KEY: source
<222> LOCATION: 1..1411
<223> OTHER INFORMATION: /mol_type="unassigned DNA"
      /organism="Saccharomyces cerevisiae"

<400> SEQUENCE: 3
ttgtaattaa aacttagatt agattgctat gctttctttc taatgagcaa gaagtaaaaa      60
aagttgtaat agaacaagaa aaatgaaact gaaacttgag aaattgaaga ccgtttatta    120
acttaaatat caatgggagg tcatcgaaag agaaaaaaat caaaaaaaaa aattttcaag    180
aaaaagaaac gtgataaaaa ttttttattgc cttttttcgac gaagaaaaag aaacgaggcg    240
gtctcttttt tcttttccaa acctttagta cgggtaatta acgacaccct agaggaagaa    300 agagggaaa tttagtatgc tgtgcttggg tgttttgaag tggtacggcg atgcgcggag    360
tccgagaaaa tctggaagag taaaaaagga gtagaaacat tttgaagcta tggtgtgtgc    420
atgcgatgga agtaccttca aagaatgggg tcttatcttg ttttgcaagt accactgagc    480
aggataataa tagaaatgat aatatactat agtagagata cgtcgatga cttcccatac    540 tgtaattgct tttagttgtg tatttttagt gtgcaagttt ctgtaaatcg attaattttt    600
ttttctttcc tcttttatt aaccttaatt tttattttag attcctgact tcaactcaag    660
acgcacagat attataacat ctgcataata ggcatttgca agaattactc gtgagtaagg    720
aaagagtgag gaactatcgc ataccctgcat ttaaagatgc cgatttgggc gcgaatcctt    780
tattttggct tcaccctcat actattatca gggccagaaa aaggaagtgt ttccctcctt    840
cttgaattga tgttaccctc ataaagcacg tggcctctta tcgagaaaga aattaccgtc    900
gctcgtgatt tgtttgcaaa aagaacaaaa ctgaaaaaac ccagacacgc tcgacttcct    960
gtcttcctat tgattgcagc ttccaattttc gtcacacaac aaggtcctag cgacggctca   1020
caggttttgt aacaagcaat cgaaggttct ggaatggcgg gaaagggttt agtaccacat   1080
gctatgatgc ccactgtgat ctccagagca aagttcgttc gatcgtactg ttactctctc   1140
tctttcaaac agaattgtcc gaatcgtgtg acaacaacag cctgttctca cacactcttt   1200
tcttctaacc aagggggtgg tttagtttag tagaaccctcg tgaaacttac atttacatat   1260
atataaactt gcataaattg gtcaatgcaa gaaatacata tttggtcttt tctaattcgt   1320 agttttcaa gttcttagat gctttctttt tctcttttt acagatcatc aaggaagtaa   1380
ttatctactt tttacaacaa atataaaaca a                                   1411

<210> SEQ ID NO 4
<211> LENGTH: 1959
<212> TYPE: DNA
<213> ORGANISM: Salmonella enterica
<220> FEATURE:
<221> NAME/KEY: source
<222> LOCATION: 1..1959
<223> OTHER INFORMATION: /mol_type="unassigned DNA"
      /organism="Salmonella enterica"

<400> SEQUENCE: 4
atgtcacaaa cacacaaaca tgctattcct gcgaatatcg ctgacaggtg cttaatcaac      60

```
cctgaacaat acgaaacgaa gtacaagcag tctatcaacg atcctgatac tttctggggc    120
gagcaaggta agatactcga ttggattact ccatatcaaa aggtcaaaaa cacatccttt    180
gctcctggaa atgtgtcaat caagtggtac gaggacggca ctctaaacct agctgctaat    240
tgcttggatc gacacctcca ggaaaatggt gacagaacgg caatcatttg gaaggtgat    300 gatacttctc aatctaagca catctcctac agagagttac acagagatgt tgcagattc    360 gcgaatactt tactggacct gggtatcaaa aagggcgatg ttgtggcaat ctacatgcct    420
atggtcccag aggcagctgt ggcaatgttg gcctgtgcca gaataggagc agtccatagc    480
gttatctttg gcggattctc ccctgaagcc gttgctggga gaatcattga ctcatcaagt    540
agattagtta tcactgccga cgaaggtgtt agagcaggta gatccatccc attgaagaaa    600
aacgttgatg acgcgttgaa aaacccaaac gttacgagtg tggagcatgt aattgtacta    660
aagcgtaccg gctctgatat agactggcag gaaggtaggg atttgtggtg gagagatctt    720
attgagaaag caagtccaga acaccaacca gaagcaatga atgcggaaga tccattgttc    780
atcttgtata catctgggtc aactggcaaa ccaaaaggtg ttttgcatac aacaggtggt    840
tatctcgtat acgccgcaac aacctttaag tacgttttt attaccatcc aggtgatatc    900
tactggtgta ccgctgatgt cggttgggtt actggtcata gttacctgct ttacggtcca    960
ctggcatgcg gcgcaaccac tttgatgttt gaaggagtac caaactggcc aaccccagcc    1020
aggatgtgtc aagtggtcga taaacaccaa gtgaacatat tgtacacagc cccaaccgcc    1080
attagagcgc taatggccga aggagataag gcgattgagg gaacagatag aagtagccta    1140
cgtatcttag gatccgttgg cgagccaatc aatccagaag cttgggaatg gtattggaaa    1200
aagattggta aggaaaagtg tccagtagtg gatacatggt ggcaaactga aacaggtgga    1260
ttcatgatta cacctcttcc agtgcaata gaattgaagg ctgggtctgc tactaggcct    1320
ttcttcggcg tccaacctgc tttagtagac aacgaagggc atccacaaga gggggcaaca    1380
gaaggcaatc tagtgataac tgattcctgg cctggtcagg ctagaacatt gtttggtgat    1440
cacgaaagat tcgaacaaac ctatttctca actttcaaaa acatgtattt cagcggtgac    1500
ggtgcgagaa gagacgaaga tgggtactac tggattaccg gcagagtaga tgacgtcctt    1560
aacgtatctg gacatcgtct gggtacagct gagattgagt cagctttagt tgctcatcct    1620
aagattgctg aagctgcagt cgttggcatc ccacacgcta tcaagggtca agccatatac    1680
gcatatgtta cactcaacca tggtgaggaa ccatctccag agctatacgc agaggtcaga    1740
aattgggttc gaaaggaaat agggccttta gccacaccag atgttttgca ttggacagat    1800
tcattgccta agacaagatc tggaaagatt atgagacgta tacttagaaa gatcgccgcc    1860
ggagatacgt ctaacttagg tgatacttct actcttgccg atccaggcgt ggtcgaaaaa    1920
cctttagagg aaaaacaagc tattgctatg ccatcatga                          1959
```

<210> SEQ ID NO 5
<211> LENGTH: 1503
<212> TYPE: DNA
<213> ORGANISM: Saccharomyces cerevisiae
<220> FEATURE:
<221> NAME/KEY: source
<222> LOCATION: 1..1503
<223> OTHER INFORMATION: /mol_type="unassigned DNA"
     /organism="Saccharomyces cerevisiae"

<400> SEQUENCE: 5

```
atgactaagc tacactttga cactgctgaa ccagtcaaga tcacacttcc aaatggtttg     60
```

| | |
|---|---|
| acatacgagc aaccaaccgg tctattcatt aacaacaagt ttatgaaagc tcaagacggt | 120 |
| aagacctatc ccgtcgaaga tccttccact gaaaacaccg tttgtgaggt ctcttctgcc | 180 |
| accactgaag atgttgaata tgctatcgaa tgtgccgacc gtgcttttcca cgacactgaa | 240 |
| tgggctaccc aagacccaag agaaagaggc cgtctactaa gtaagttggc tgacgaattg | 300 |
| gaaagccaaa ttgacttggt ttcttccatt gaagctttgg acaatggtaa aactttggcc | 360 |
| ttagcccgtg gggatgttac cattgcaatc aactgtctaa gagatgctgc tgcctatgcc | 420 |
| gacaaagtca acggtagaac aatcaacacc ggtgacggct acatgaactt caccacctta | 480 |
| gagccaatcg gtgtctgtgg tcaaattatt ccatggaact ttccaataat gatgttggct | 540 |
| tggaagatcg ccccagcatt ggccatgggt aacgtctgta tcttgaaacc cgctgctgtc | 600 |
| acacctttaa atgccctata ctttgcttct ttatgtaaga aggttggtat tccagctggt | 660 |
| gtcgtcaaca tcgttccagg tcctggtaga actgttggtg ctgctttgac caacgaccca | 720 |
| agaatcagaa agctggcttt taccggttct acagaagtcg gtaagagtgt tgctgtcgac | 780 |
| tcttctgaat ctaacttgaa gaaaatcact ttggaactag gtgtaagtc cgcccatttg | 840 |
| gtctttgacg atgctaacat taagaagact ttaccaaatc tagtaaacgg tattttcaag | 900 |
| aacgctggtc aaatttgttc ctctggttct agaatttacg ttcaagaagg tatttacgac | 960 |
| gaactattgg ctgctttcaa ggcttacttg gaaaccgaaa tcaaagttgg taatccatttt | 1020 |
| gacaaggcta acttccaagg tgctatcact aaccgtcaac aattcgacac aattatgaac | 1080 |
| tacatcgata tcggtaagaa agaaggcgcc aagatcttaa ctggtggcga aaaagttggt | 1140 |
| gacaagggtt acttcatcag accaaccgtt ttctacgatg ttaatgaaga catgagaatt | 1200 |
| gttaaggaag aaattttggg accagttgtc actgtcgcaa agttcaagac tttagaagaa | 1260 |
| ggtgtcgaaa tggctaacag ctctgaattc ggtctaggtt ctggtatcga aacagaatct | 1320 |
| ttgagcacag gtttgaaggt ggccaagatg ttgaaggccg gtaccgtctg gatcaacaca | 1380 |
| tacaacgatt ttgactccag agttccattc ggtggtgtta agcaatctgg ttacggtaga | 1440 |
| gaaatgggtg aagaagtcta ccatgcatac actgaagtaa aagctgtcag aattaagttg | 1500 |
| tga | 1503 |

<210> SEQ ID NO 6
<211> LENGTH: 1692
<212> TYPE: DNA
<213> ORGANISM: Saccharomyces cerevisiae
<220> FEATURE:
<221> NAME/KEY: source
<222> LOCATION: 1..1692
<223> OTHER INFORMATION: /mol_type="unassigned DNA"
      /organism="Saccharomyces cerevisiae"

<400> SEQUENCE: 6

| | |
|---|---|
| atgtctgaaa ttactttggg taaatatttg ttcgaaagat aaagcaagt caacgttaac | 60 |
| accgttttcg gtttgccagg tgacttcaac ttgtccttgt tggacaagat ctacgaagtt | 120 |
| gaaggtatga gatgggctgg taacgccaac gaattgaacg ctgcttacgc cgctgatggt | 180 |
| tacgctcgta tcaagggtat gtcttgtatc atcaccacct tcggtgtcgg tgaattgtct | 240 |
| gctttgaacg gtattgccgg ttcttacgct gaacacgtcg gtgttttgca cgttgttggt | 300 |
| gtcccatcca tctctgctca agctaagcaa ttgttgttgc accacacctt gggtaacggt | 360 |
| gacttcactg ttttccacag aatgtctgcc aacatttctg aaaccactgc tatgatcact | 420 |
| gacattgcta ccgccccagc tgaaattgac agatgtatca gaaccactta cgtcacccaa | 480 |

| | |
|---|---|
| agaccagtct acttaggttt gccagctaac ttggtcgact tgaacgtccc agctaagttg | 540 |
| ttgcaaactc caattgacat gtctttgaag ccaaacgatg ctgaatccga aaaggaagtc | 600 |
| attgacacca tcttggcttt ggtcaaggat gctaagaacc cagttatctt ggctgatgct | 660 |
| tgttgttcca gacacgacgt caaggctgaa actaagaagt tgattgactt gactcaattc | 720 |
| ccagctttcg tcaccccaat gggtaagggt tccattgacg aacaacaccc aagatacggt | 780 |
| ggtgtttacg tcggtacctt gtccaagcca gaagttaagg aagccgttga atctgctgac | 840 |
| ttgattttgt ctgtcggtgc tttgttgtct gatttcaaca ccggttcttt ctcttactct | 900 |
| tacaagacca agaacattgt cgaattccac tccgaccaca tgaagatcag aaacgccact | 960 |
| ttcccaggtg tccaaatgaa attcgttttg caaaagttgt tgaccactat tgctgacgcc | 1020 |
| gctaagggtt acaagccagt tgctgtccca gctagaactc cagctaacgc tgctgtccca | 1080 |
| gcttctaccc cattgaagca agaatggatg tggaaccaat tgggtaactt cttgcaagaa | 1140 |
| ggtgatgttg tcattgctga aaccggtacc tccgctttcg gtatcaacca aaccactttc | 1200 |
| ccaaacaaca cctacggtat ctctcaagtc ttatggggtt ccattggttt caccactggt | 1260 |
| gctaccttgg gtgctgcttt cgctgctgaa gaaattgatc aaagaagag agttatctta | 1320 |
| ttcattggtg acggttcttt gcaattgact gttcaagaaa tctccaccat gatcagatgg | 1380 |
| ggcttgaagc catacttgtt cgtcttgaac aacgatggtt acaccattga aaagttgatt | 1440 |
| cacggtccaa aggctcaata aacgaaatt caaggttggg accacctatc cttgttgcca | 1500 |
| actttcggtg ctaaggacta tgaaacccac agagtcgcta ccaccggtga atgggacaag | 1560 |
| ttgacccaag acaagtcttt caacgacaac tctaagatca gaatgattga aatcatgttg | 1620 |
| ccagtcttcg atgctccaca aaacttggtt gaacaagcta agttgactgc tgctaccaac | 1680 |
| gctaagcaat aa | 1692 |

```
<210> SEQ ID NO 7
<211> LENGTH: 420
<212> TYPE: DNA
<213> ORGANISM: Saccharomyces cerevisiae
<220> FEATURE:
<221> NAME/KEY: source
<222> LOCATION: 1..420
<223> OTHER INFORMATION: /mol_type="unassigned DNA"
      /organism="Saccharomyces cerevisiae"

<400> SEQUENCE: 7
```

| | |
|---|---|
| gcacacacca tagcttcaaa atgtttctac tcctttttta ctcttccaga ttttctcgga | 60 |
| ctccgcgcat cgccgtacca cttcaaaaca cccaagcaca gcatactaaa tttcccctct | 120 |
| ttcttcctct agggtgtcgt taattacccg tactaaaggt ttggaaaaga aaaagagac | 180 |
| cgcctcgttt ctttttcttc gtcgaaaaag gcaataaaaa ttttatcac gtttcttttt | 240 |
| cttgaaaatt ttttttttg atttttttct ctttcgatga cctcccattg atatttaagt | 300 |
| taataaacgg tcttcaattt ctcaagtttc agtttcattt tcttgttct attacaactt | 360 |
| tttttacttc ttgctcatta gaaagaaagc atagcaatct aatctaagtt ttaattacaa | 420 |

```
<210> SEQ ID NO 8
<211> LENGTH: 1005
<212> TYPE: DNA
<213> ORGANISM: Clostridium acetobutylicum
<220> FEATURE:
<221> NAME/KEY: source
<222> LOCATION: 1..1005
<223> OTHER INFORMATION: /mol_type="unassigned DNA"
      /organism="Clostridium acetobutylicum"
```

<400> SEQUENCE: 8

```
atggcaaaga tagctattaa tggttttgga agaataggaa gattagcttt aagaagaatt      60
cttgaagtac ctggattgga agttgttgca ataaacgact taactgatgc aaaaatgtta     120
gcacacttat ttaaatatga ttcatcacaa ggaagattca atggagaaat tgaagttaaa     180
gaaggagctt tcgtagtaaa cggaaaagaa gttaaagttt tcgctgaagc agatcctgaa     240
aaattacctt ggggagatct tggaatagac gttgttcttg agtgcacagg tttcttcaca     300
aagaaagaaa aagcagaagc tcacgtaaga gcaggcgcta aaaagttgt tatatcagct      360
ccagctggaa acgacttaaa gacaatagtt ttcaacgtta ataatgaaga tcttgatgga     420
acagaaacag ttatatcagg tgcatcatgc acaactaact gcttagctcc aatggctaaa     480
gtattaaatg ataaatttgg aatagaaaaa ggattcatga ctacaattca tgcgttcact     540
aatgaccaaa acacattaga tggtccacac agaaaggag atttaagaag agctagagct      600
gctgctgtaa gtatcatccc taactcaact ggtgctgcta agctataag ccaagttatt      660
cctgacttag ctggaaaatt agacggaaac gctcaaagag ttccagttcc aactggttca     720
ataactgaat tagtttcagt tcttaagaaa aagttacag ttgaagaaat caacgctgct      780
atgaaagaag ctgctgatga atcatttgga tacactgaag atccaatcgt ttcagctgac     840
gtagtaggaa tcaactacgg atcattattt gatgcaactt taactaaaat tgttgatgtt     900
aacggatcac aattagttaa aacagctgct tggtatgata tgaaatgtc atacacttca      960
caattagtta gaactttagc ttactttgca aaaatagcaa aatag                    1005
```

<210> SEQ ID NO 9
<211> LENGTH: 1071
<212> TYPE: DNA
<213> ORGANISM: Kluyveromyces lactis
<220> FEATURE:
<221> NAME/KEY: source
<222> LOCATION: 1..1071
<223> OTHER INFORMATION: /mol_type="unassigned DNA"
       /organism="Kluyveromyces lactis"

<400> SEQUENCE: 9

```
atgccagaca tgacaaatga atcaagtagt aagccagcac aaatcaacat cggtatcaac      60
ggtttcggta gaataggtag attggtattg agagctgcat taacccatcc tgaagtcaaa     120
gtaagattga ttaataaccc atctactaca cctgaatacg ccgcttattt gtttaaatac     180
gattcaacac acggtaaata cagaggtgaa gtcgaattcg atgacgaaag aatcatcatc     240
caaaacgatc atgtttccgc acacattcca ttgagtcatt ttagagaacc agaaagaata     300
ccttgggcct cttataacgt tgattacgtc attgactcaa ccggtgtttt caaagaagtc     360
gatactgctt ccagacacaa gggtgttaag aaagttatta tcactgcacc atctaagaca     420
gcccctatgt atgtctacgg tgtaaaccat gttaagtaca acccttgac tgatcacgtt      480
gtctctaatg cttcatgtac cactaactgc ttggctccat tagttaaagc attggatgac     540
gaattcggta tcgaagaagc attgatgaca accatccatg ccactacagc ttctcaaaag     600
actgttgatg gtacttcttc tggtggtaaa gactggagag tggtagatc atgtcaaggt      660
aatatcattc catccagtac tggtgcagcc aaagctgttg gtaaaatatt gcctgaatta     720
aacggtaaaa tcacaggcat gtccataaga gtaccaacca taaacatcag tttggttgat     780
ttgacctta gaactgccaa aaagacatct tacgatgaca taatgaaggc tttgaacaa      840
agatctagat cagatatgaa aggtgtctta ggtgtaacta aggacgcagt agtttcttca     900
```

```
gatttcacat ccgacagtag atccagtatc gttgatgcta aagcaggtat agaattgaac    960
gaccatttct ttaaggtttt gtcttggtac gataacgaat atggttacag ttccagagta  1020
gtagacttga gtatattcat ggcacaaaag gatttcgaag caggtgtata a            1071
```

<210> SEQ ID NO 10
<211> LENGTH: 1023
<212> TYPE: DNA
<213> ORGANISM: Bacillus subtilis
<220> FEATURE:
<221> NAME/KEY: source
<222> LOCATION: 1..1023
<223> OTHER INFORMATION: /mol_type="unassigned DNA"
      /organism="Bacillus subtilis"

<400> SEQUENCE: 10

```
atgaaggtta aggttgccat caacggtttc ggtagaattg gtagaatggt tttcagaaag     60
gccatgttgg atgatcaaat tcaagttgtt gctatcaacg cttcctactc tgctgaaact    120
ttggctcatt tgattaagta cgataccatc cacggtagat acgacaaaga agttgtagct    180
ggtgaagatt ccttgatcgt taatggtaag aaggtcttgt tgttgaactc cagagatcca    240
aaacaattgc cttggagaga atacgatatt gacatcgttg ttgaagctac tggtaagttt    300
aacgctaagg ataaggctat gggtcatatt gaagctggtg ctaagaaggt tatttttgact   360 gctccaggta agaacgaaga tgttactata gttatgggtg tcaacgaaga tcaattcgat    420
gctgaaagac acgttattat ctctaacgct tcttgtacca ctaactgttt ggctccagtt    480
gttaaggttt tggacgaaga atttggtatc gaatctggtt tgatgactac cgttcatgct    540
tacaccaatg accaaaagaa cattgataac ccacacaagg atttgagaag agctagagct    600
tgtggtgaat ctattattcc aactactact ggtgctgcta aggctttgtc tttggttttg    660
ccacatttga agggtaaatt gcatggtttg ctttgagag ttccagttcc aaatgtttcc     720
ttggttgatt tggttgtcga tttgaaaact gatgttaccg ccgaagaagt taacgaagcc    780
tttaaaagag ctgctaagac ttctatgtat ggtgtcttgg attactccga tgaaccattg    840
gtttctactg attacaacac caatccacat tccgctgtta ttgatggttt gaccactatg    900
gttatggaag atagaaaggt caaagttttg gcctggtacg ataatgaatg gggttattct    960
tgtagagtcg tcgacttgat tagacatgtt gctgctagaa tgaagcaccc atctgctgtt   1020
taa                                                                 1023
```

<210> SEQ ID NO 11
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer"
      /organism="Artificial Sequence"

<400> SEQUENCE: 11
cgtgcgautc atttcaaagt cttcaacaat tt                                   32

<210> SEQ ID NO 12
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer"
      /organism="Artificial Sequence"

<400> SEQUENCE: 12
agtgcaggua aaacaatgag cgaagaaagc tta                         33

<210> SEQ ID NO 13
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer"
      /organism="Artificial Sequence"

<400> SEQUENCE: 13
atctgtcaua aaacaatgag tggtacaggt ag                          32

<210> SEQ ID NO 14
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer"
      /organism="Artificial Sequence"

<400> SEQUENCE: 14
cacgcgautc agactgtaat ggctctacct c                           31

<210> SEQ ID NO 15
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer"
      /organism="Artificial Sequence"

<400> SEQUENCE: 15
acctgcacut tgtaattaaa acttag                                 26

<210> SEQ ID NO 16
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="unassigned DNA"
      /note="Primer"
      /organism="Artificial Sequence"

<400> SEQUENCE: 16
atgacagaut tgttttatat ttgttg                                 26

<210> SEQ ID NO 17
<211> LENGTH: 35
<212> TYPE: DNA
<213> ORGANISM: Artificial Sequence
<220> FEATURE:

```
<221> NAME/KEY: source
<222> LOCATION: 1..35
<223> OTHER INFORMATION: /mol_type="unassigned DNA"
      /note="Primer"
      /organism="Artificial Sequence"

<400> SEQUENCE: 17
atttgcggcc gctttagttt ctaccatgag cgaag                          35

<210> SEQ ID NO 18
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Primer"
      /organism="Artificial Sequence"

<400> SEQUENCE: 18
ggcgagctcg caaggtttat ttcaaagtct t                              31

<210> SEQ ID NO 19
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer"
      /organism="Artificial Sequence"

<400> SEQUENCE: 19
catatgacaa atctgaaaca gcaacagccc tgttcatacc                     40

<210> SEQ ID NO 20
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer"
      /organism="Artificial Sequence"

<400> SEQUENCE: 20
ggtatgaaca gggctgttgc tgtttcagat ttgtcatatg                     40

<210> SEQ ID NO 21
<211> LENGTH: 40
<212> TYPE: DNA
<213> ORGANISM: Artificial Sequence
<220> FEATURE:
<221> NAME/KEY: source
<222> LOCATION: 1..40
<223> OTHER INFORMATION: /mol_type="unassigned DNA"
      /note="Primer"
      /organism="Artificial Sequence"

<400> SEQUENCE: 21
atggcaatca aaagaccacc atcagctagt tgacgcagta                     40

<210> SEQ ID NO 22
<211> LENGTH: 40
<212> TYPE: DNA
<213> ORGANISM: Artificial Sequence
```

```
<220> FEATURE:
<221> NAME/KEY: source
<222> LOCATION: 1..40
<223> OTHER INFORMATION: /mol_type="unassigned DNA"
      /note="Primer"
      /organism="Artificial Sequence"

<400> SEQUENCE: 22
tactgcgtca actagctgat ggtggtcttt tgattgccat                              40

<210> SEQ ID NO 23
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Primer"
      /organism="Artificial Sequence"

<400> SEQUENCE: 23
agtgcaggua aaacaatgtc acaaacacac                                        30

<210> SEQ ID NO 24
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer"
      /organism="Artificial Sequence"

<400> SEQUENCE: 24
cgtgcgautc atgatggcat agcaatag                                          28

<210> SEQ ID NO 25
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Primer"
      /organism="Artificial Sequence"

<400> SEQUENCE: 25
atctgtcaua aaacaatgac taagctacac tttgacac                               38

<210> SEQ ID NO 26
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer"
      /organism="Artificial Sequence"

<400> SEQUENCE: 26
cacgcgautc acaacttaat tctgacagct tttac                                  35

<210> SEQ ID NO 27
<211> LENGTH: 45
<212> TYPE: DNA
```

```
<213> ORGANISM: Artificial Sequence
<220> FEATURE:
<221> NAME/KEY: source
<222> LOCATION: 1..45
<223> OTHER INFORMATION: /mol_type="unassigned DNA"
      /note="Primer"
      /organism="Artificial Sequence"

<400> SEQUENCE: 27
agtgcaggua aaacaatgtc tgaaattact ttgggtaaat atttg          45

<210> SEQ ID NO 28
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer"
      /organism="Artificial Sequence"

<400> SEQUENCE: 28
cgtgcgautc attgcttagc gttggtagca gcagtc                    36

<210> SEQ ID NO 29
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Primer"
      /organism="Artificial Sequence"

<400> SEQUENCE: 29
cacgcgaugc acacaccata gcttc                                25
```